United States Patent
Perler et al.

(10) Patent No.: US 11,931,106 B2
(45) Date of Patent: Mar. 19, 2024

(54) PATIENT-SPECIFIC SURGICAL METHODS AND INSTRUMENTATION

(71) Applicant: TREACE MEDICAL CONCEPTS, INC., Ponte Vedra, FL (US)

(72) Inventors: Adam D. Perler, St. Petersburg, FL (US); James Q. Spitler, Winter Garden, FL (US)

(73) Assignee: Treace Medical Concepts, Inc., Ponte Vedra, FL (US)

( * ) Notice: Subject to any disclaimer, the term of this patent is extended or adjusted under 35 U.S.C. 154(b) by 430 days.

(21) Appl. No.: 17/020,630

(22) Filed: Sep. 14, 2020

(65) Prior Publication Data
US 2021/0077192 A1   Mar. 18, 2021

Related U.S. Application Data

(60) Provisional application No. 62/900,294, filed on Sep. 13, 2019.

(51) Int. Cl.
*A61B 17/17* (2006.01)
*A61B 17/15* (2006.01)
(Continued)

(52) U.S. Cl.
CPC ............ *A61B 34/10* (2016.02); *A61B 17/152* (2013.01); *A61B 17/1775* (2016.11);
(Continued)

(58) Field of Classification Search
CPC .......... A61B 17/1775; A61B 2017/565; A61B 17/151; A61B 17/8095; A61B 17/152;
(Continued)

(56) References Cited

U.S. PATENT DOCUMENTS 3,664,022 A   5/1972   Small
4,069,824 A   1/1978   Weinstock
(Continued)

FOREIGN PATENT DOCUMENTS

AU   2009222469 B2   2/2015
AU   2015203808 B2   9/2017
(Continued)

OTHER PUBLICATIONS

International Search Report and Written Opinion dated Dec. 17, 2020 for corresponding International Application No. PCT/US2020/050764.
(Continued)

*Primary Examiner* — Samuel S Hanna
(74) *Attorney, Agent, or Firm* — Maywood IP Law; David McKenzie; David Meibos

(57) ABSTRACT

A method may be used to correct a condition present in a patient. The method may include obtaining a first bone model of a first bone of one or more bones of the patient's foot, and using at least the first bone model to generate a cutting guide model. The cutting guide model may define a first bone engagement surface shaped to match a first contour on the first bone, and a first guide feature that, with the first bone engagement surface overlying the first contour, is positioned to guide resection of the one or more bones as part of a surgical osteotomy for correcting the condition. The surgical procedure may be selected from a first group consisting of a bunion correction osteotomy, an Evans calcaneal osteotomy, and a medializing calcaneal osteotomy. The first bone may be selected from a second group consisting a metatarsus, a cuneiform, and a calcaneus.

10 Claims, 13 Drawing Sheets

(51) Int. Cl.

| | |
|---|---|
| *A61B 34/10* | (2016.01) |
| *G06F 30/10* | (2020.01) |
| *G06T 7/00* | (2017.01) |
| *G06T 11/00* | (2006.01) |
| *G16H 20/40* | (2018.01) |
| *G16H 30/20* | (2018.01) |
| *G16H 30/40* | (2018.01) |
| *G16H 50/50* | (2018.01) |
| *A61B 17/00* | (2006.01) |
| *A61B 17/56* | (2006.01) |
| *A61B 90/00* | (2016.01) |
| *G06Q 50/04* | (2012.01) |

(52) U.S. Cl.
CPC ............ *G06F 30/10* (2020.01); *G06T 7/0012* (2013.01); *G06T 11/008* (2013.01); *G16H 20/40* (2018.01); *G16H 30/20* (2018.01); *G16H 30/40* (2018.01); *G16H 50/50* (2018.01); *A61B 2017/00526* (2013.01); *A61B 2017/565* (2013.01); *A61B 2034/105* (2016.02); *A61B 2034/108* (2016.02); *A61B 2090/3762* (2016.02); *G06Q 50/04* (2013.01); *G06T 2207/10081* (2013.01); *G06T 2207/30008* (2013.01)

(58) Field of Classification Search
CPC .............. A61B 17/56; A61B 2017/568; A61B 2034/105; A61B 2034/108; A61B 2017/00526; A61B 34/10; A61B 2034/102; A61B 2090/3762
See application file for complete search history.

(56) References Cited

U.S. PATENT DOCUMENTS

| | | | |
|---|---|---|---|
| 4,159,716 A | 7/1979 | Borchers | |
| 4,187,840 A | 2/1980 | Watanabe | |
| 4,335,715 A | 6/1982 | Kirkley | |
| 4,338,927 A | 7/1982 | Volkov et al. | |
| 4,349,018 A | 9/1982 | Chambers | |
| 4,409,973 A | 10/1983 | Neufeld | |
| 4,436,684 A | 3/1984 | White | |
| 4,440,168 A | 4/1984 | Warren | |
| 4,501,268 A | 2/1985 | Comparetto | |
| 4,502,474 A | 3/1985 | Comparetto | |
| 4,509,511 A | 4/1985 | Neufeld | |
| 4,565,191 A | 1/1986 | Slocum | |
| 4,570,624 A | 2/1986 | Wu | |
| 4,627,425 A | 12/1986 | Reese | |
| 4,628,919 A | 12/1986 | Clyburn | |
| 4,632,102 A | 12/1986 | Comparetto | |
| 4,664,102 A | 5/1987 | Comparetto | |
| 4,708,133 A | 11/1987 | Comparetto | |
| 4,736,737 A | 4/1988 | Fargie et al. | |
| 4,750,481 A | 6/1988 | Reese | |
| 4,754,746 A | 7/1988 | Cox | |
| 4,757,810 A | 7/1988 | Reese | |
| 4,839,822 A | 6/1989 | Dormond et al. | |
| 4,895,141 A | 1/1990 | Koeneman et al. | |
| 4,952,214 A | 8/1990 | Comparetto | |
| 4,959,066 A | 9/1990 | Dunn et al. | |
| 4,978,347 A | 12/1990 | Ilizarov | |
| 4,988,349 A | 1/1991 | Pennig | |
| 4,995,875 A | 2/1991 | Coes | |
| 5,021,056 A | 6/1991 | Hofmann et al. | |
| 5,035,698 A | 7/1991 | Comparetto | |
| 5,042,983 A | 8/1991 | Rayhack | |
| 5,049,149 A | 9/1991 | Schmidt | |
| 5,053,039 A | 10/1991 | Hofmann et al. | |
| 5,078,719 A | 1/1992 | Schreiber | |
| 5,112,334 A | 5/1992 | Alchermes et al. | |
| 5,147,364 A | 9/1992 | Comparetto | |
| 5,176,685 A | 1/1993 | Rayhack | |
| 5,207,676 A | 5/1993 | Canadell et al. | |
| 5,246,444 A | 9/1993 | Schreiber | |
| 5,254,119 A | 10/1993 | Schreiber | |
| 5,312,412 A | 5/1994 | Whipple | |
| 5,358,504 A | 10/1994 | Paley et al. | |
| 5,364,402 A | 11/1994 | Mumme et al. | |
| 5,374,271 A | 12/1994 | Hwang | |
| 5,413,579 A | 5/1995 | Toit | |
| 5,417,694 A | 5/1995 | Marik et al. | |
| 5,449,360 A | 9/1995 | Schreiber | |
| 5,470,335 A | 11/1995 | Du Toit | |
| 5,490,854 A | 2/1996 | Fisher et al. | |
| 5,529,075 A | 6/1996 | Clark | |
| 5,540,695 A | 7/1996 | Levy | |
| 5,578,038 A | 11/1996 | Slocum | |
| 5,586,564 A | 12/1996 | Barrett et al. | |
| 5,601,565 A | 2/1997 | Huebner | |
| 5,613,969 A | 3/1997 | Jenkins, Jr. | |
| 5,620,442 A | 4/1997 | Bailey et al. | |
| 5,620,448 A | 4/1997 | Puddu | |
| 5,643,270 A | 7/1997 | Combs | |
| 5,667,510 A | 9/1997 | Combs | |
| H1706 H | 1/1998 | Mason | |
| 5,722,978 A | 3/1998 | Jenkins | |
| 5,749,875 A | 5/1998 | Puddu | |
| 5,779,709 A | 7/1998 | Harris et al. | |
| 5,788,695 A | 8/1998 | Richardson | |
| 5,803,924 A | 9/1998 | Oni et al. | |
| 5,810,822 A | 9/1998 | Mortier | |
| 5,839,438 A | 11/1998 | Graettinger et al. | |
| 5,843,085 A | 12/1998 | Graser | |
| 5,893,553 A | 4/1999 | Pinkous | |
| 5,911,724 A | 6/1999 | Wehrli | |
| 5,935,128 A | 8/1999 | Carter et al. | |
| 5,941,877 A | 8/1999 | Viegas et al. | |
| 5,951,556 A | 9/1999 | Faccioli et al. | |
| 5,980,526 A | 11/1999 | Johnson et al. | |
| 5,984,931 A | 11/1999 | Greenfield | |
| 6,007,535 A | 12/1999 | Rayhack et al. | |
| 6,027,504 A | 2/2000 | Mcguire | |
| 6,030,391 A | 2/2000 | Brainard et al. | |
| 6,162,223 A | 12/2000 | Orsak et al. | |
| 6,171,309 B1 | 1/2001 | Huebner | |
| 6,203,545 B1 | 3/2001 | Stoffella | |
| 6,248,109 B1 | 6/2001 | Stoffella | |
| 6,391,031 B1 | 5/2002 | Toomey | |
| 6,416,465 B2 | 7/2002 | Brau | |
| 6,478,799 B1 | 11/2002 | Williamson | |
| 6,511,481 B2 | 1/2003 | von Hoffmann et al. | |
| 6,547,793 B1 | 4/2003 | McGuire | |
| 6,676,662 B1 | 1/2004 | Bagga et al. | |
| 6,719,773 B1 | 4/2004 | Boucher et al. | |
| 6,743,233 B1 | 6/2004 | Baldwin et al. | |
| 6,755,838 B2 | 6/2004 | Trnka | |
| 6,796,986 B2 | 9/2004 | Duffner | |
| 6,859,661 B2 | 2/2005 | Tuke | |
| 6,944,518 B2 | 9/2005 | Roose | |
| 6,964,645 B1 | 11/2005 | Smits | |
| 7,018,383 B2 | 3/2006 | McGuire | |
| 7,033,361 B2 | 4/2006 | Collazo | |
| 7,097,647 B2 | 8/2006 | Segler et al. | |
| 7,112,204 B2 | 9/2006 | Justin et al. | |
| 7,153,310 B2 | 12/2006 | Ralph et al. | |
| 7,182,766 B1 | 2/2007 | Mogul | |
| 7,241,298 B2 | 7/2007 | Nemec et al. | |
| 7,282,054 B2 | 10/2007 | Steffensmeier et al. | |
| 7,351,203 B2 | 4/2008 | Jelliffe et al. | |
| 7,377,924 B2 | 5/2008 | Raistrick et al. | |
| 7,465,303 B2 | 12/2008 | Riccione et al. | |
| 7,540,874 B2 | 6/2009 | Trumble et al. | |
| 7,572,258 B2 | 8/2009 | Stiernborg | |
| 7,618,451 B2 | 11/2009 | Berez et al. | |
| 7,641,660 B2 | 1/2010 | Lakin et al. | |
| D610,257 S | 2/2010 | Horton | |
| 7,686,811 B2 | 3/2010 | Byrd et al. | |
| 7,691,108 B2 | 4/2010 | Lavallee | |
| 7,763,026 B2 | 7/2010 | Egger et al. | |
| D629,900 S | 12/2010 | Fisher | |

(56) References Cited

U.S. PATENT DOCUMENTS

| | | |
|---|---|---|
| 7,967,823 B2 | 6/2011 | Ammann et al. |
| 7,972,338 B2 | 7/2011 | O'Brien |
| D646,389 S | 10/2011 | Claypool et al. |
| 8,057,478 B2 | 11/2011 | Kuczynski et al. |
| 8,062,301 B2 | 11/2011 | Ammann et al. |
| D651,315 S | 12/2011 | Bertoni et al. |
| D651,316 S | 12/2011 | May et al. |
| 8,080,010 B2 | 12/2011 | Schulz et al. |
| 8,080,045 B2 | 12/2011 | Wotton, III |
| 8,083,745 B2 | 12/2011 | Lang et al. |
| 8,083,746 B2 | 12/2011 | Novak |
| 8,105,330 B2 | 1/2012 | Fitz et al. |
| 8,123,753 B2 | 2/2012 | Poncet |
| 8,137,406 B2 | 3/2012 | Novak et al. |
| 8,147,530 B2 | 4/2012 | Strnad et al. |
| 8,160,345 B2 | 4/2012 | Pavlovskaia et al. |
| 8,167,918 B2 | 5/2012 | Strnad et al. |
| 8,172,848 B2 | 5/2012 | Tomko et al. |
| 8,192,441 B2 | 6/2012 | Collazo |
| 8,197,487 B2 | 6/2012 | Poncet et al. |
| 8,231,623 B1 | 7/2012 | Jordan |
| 8,231,663 B2 | 7/2012 | Kay et al. |
| 8,236,000 B2 | 8/2012 | Ammann et al. |
| 8,246,561 B1 | 8/2012 | Agee et al. |
| 8,246,680 B2 | 8/2012 | Betz et al. |
| D666,721 S | 9/2012 | Wright et al. |
| 8,262,664 B2 | 9/2012 | Justin et al. |
| 8,277,459 B2 | 10/2012 | Sand et al. |
| 8,282,644 B2 | 10/2012 | Edwards |
| 8,282,645 B2 | 10/2012 | Lawrence et al. |
| 8,292,966 B2 | 10/2012 | Morton |
| 8,298,237 B2 | 10/2012 | Schoenefeld et al. |
| 8,303,596 B2 | 11/2012 | Plassky et al. |
| 8,313,492 B2 | 11/2012 | Wong et al. |
| 8,323,288 B2 | 12/2012 | Zajac |
| 8,323,289 B2 | 12/2012 | Re |
| 8,337,501 B2 | 12/2012 | Fitz et al. |
| 8,337,503 B2 | 12/2012 | Lian |
| 8,343,159 B2 | 1/2013 | Bennett |
| 8,366,771 B2 | 2/2013 | Burdulis, Jr. et al. |
| 8,377,105 B2 | 2/2013 | Buescher |
| D679,395 S | 4/2013 | Wright et al. |
| 8,409,209 B2 | 4/2013 | Ammann et al. |
| 8,435,246 B2 | 5/2013 | Fisher et al. |
| 8,475,462 B2 | 7/2013 | Thomas et al. |
| 8,475,463 B2 | 7/2013 | Lian |
| 8,484,001 B2 | 7/2013 | Glozman et al. |
| 8,496,662 B2 | 7/2013 | Novak et al. |
| 8,518,045 B2 | 8/2013 | Szanto |
| 8,523,870 B2 | 9/2013 | Green et al. |
| 8,529,571 B2 | 9/2013 | Horan et al. |
| 8,540,777 B2 | 9/2013 | Ammann et al. |
| 8,545,508 B2 | 10/2013 | Collazo |
| 8,551,102 B2 | 10/2013 | Fitz et al. |
| 8,556,906 B2 | 10/2013 | Fitz et al. |
| 8,561,278 B2 | 10/2013 | Fitz et al. |
| 8,585,708 B2 | 11/2013 | Fitz et al. |
| D694,884 S | 12/2013 | Mooradian et al. |
| D695,402 S | 12/2013 | Dacosta et al. |
| 8,634,617 B2 | 1/2014 | Tsougarakis et al. |
| 8,652,142 B2 | 2/2014 | Geissler |
| 8,657,820 B2 | 2/2014 | Kubiak et al. |
| 8,657,827 B2 | 2/2014 | Fitz et al. |
| D701,303 S | 3/2014 | Cook |
| 8,672,945 B2 | 3/2014 | Lavallee et al. |
| 8,682,052 B2 | 3/2014 | Fitz et al. |
| 8,696,716 B2 | 4/2014 | Kartalian et al. |
| 8,702,686 B2 | 4/2014 | Geebelen et al. |
| 8,702,715 B2 | 4/2014 | Ammann et al. |
| D705,929 S | 5/2014 | Frey |
| 8,715,363 B2 | 5/2014 | Ratron et al. |
| 8,728,084 B2 | 5/2014 | Berelsman et al. |
| 8,758,354 B2 | 6/2014 | Habegger et al. |
| 8,764,760 B2 | 7/2014 | Metzger et al. |
| 8,764,763 B2 | 7/2014 | Wong et al. |
| 8,768,028 B2 | 7/2014 | Lang et al. |
| 8,771,279 B2 | 7/2014 | Philippon et al. |
| 8,777,948 B2 | 7/2014 | Bernsteiner |
| 8,784,427 B2 | 7/2014 | Fallin et al. |
| 8,784,457 B2 | 7/2014 | Graham |
| 8,795,286 B2 | 8/2014 | Sand et al. |
| 8,801,719 B2 | 8/2014 | Park et al. |
| 8,801,727 B2 | 8/2014 | Chan et al. |
| 8,808,301 B1 | 8/2014 | Nofsinger |
| 8,808,303 B2 | 8/2014 | Stemniski et al. |
| 8,821,499 B2 | 9/2014 | Iannotti et al. |
| 8,828,012 B2 | 9/2014 | May et al. |
| 8,828,063 B2 | 9/2014 | Blitz et al. |
| 8,838,263 B2 | 9/2014 | Sivak et al. |
| 8,858,602 B2 | 10/2014 | Weiner et al. |
| 8,882,778 B2 | 11/2014 | Ranft |
| 8,882,816 B2 | 11/2014 | Kartalian et al. |
| 8,888,785 B2 | 11/2014 | Ammann et al. |
| D720,456 S | 12/2014 | Dacosta et al. |
| 8,900,247 B2 | 12/2014 | Tseng et al. |
| 8,906,026 B2 | 12/2014 | Ammann et al. |
| 8,945,132 B2 | 2/2015 | Plassy et al. |
| 8,965,088 B2 | 2/2015 | Tsougarakis et al. |
| 8,983,813 B2 | 3/2015 | Miles et al. |
| 8,998,903 B2 | 4/2015 | Price et al. |
| 8,998,904 B2 | 4/2015 | Zeetser et al. |
| 9,011,452 B2 | 4/2015 | Iannotti et al. |
| 9,014,835 B2 | 4/2015 | Azernikov et al. |
| 9,017,336 B2 | 4/2015 | Park et al. |
| 9,023,052 B2 | 5/2015 | Lietz et al. |
| 9,044,250 B2 | 6/2015 | Olsen et al. |
| 9,055,953 B2 | 6/2015 | Lang et al. |
| 9,060,822 B2 | 6/2015 | Lewis et al. |
| 9,066,727 B2 | 6/2015 | Catanzarite et al. |
| 9,089,376 B2 | 7/2015 | Medoff et al. |
| 9,095,353 B2 | 8/2015 | Burdulis et al. |
| 9,101,421 B2 | 8/2015 | Blacklidge |
| 9,107,715 B2 | 8/2015 | Blitz et al. |
| 9,113,920 B2 | 8/2015 | Ammann et al. |
| 9,131,945 B2 | 9/2015 | Aram et al. |
| D740,424 S | 10/2015 | Dacosta et al. |
| 9,186,154 B2 | 11/2015 | Li |
| 9,198,678 B2 | 12/2015 | Frey et al. |
| 9,216,025 B2 | 12/2015 | Fitz et al. |
| 9,220,509 B2 | 12/2015 | Boyer et al. |
| 9,289,221 B2 | 3/2016 | Gelaude et al. |
| 9,351,744 B2 | 5/2016 | Kunz et al. |
| 9,358,019 B2 | 6/2016 | Gibson et al. |
| 9,361,410 B2 | 6/2016 | Davison et al. |
| 9,402,636 B2 | 8/2016 | Collazo |
| 9,402,640 B2 | 8/2016 | Reynolds et al. |
| 9,411,939 B2 | 8/2016 | Furrer et al. |
| 9,414,847 B2 | 8/2016 | Kurtz |
| D765,844 S | 9/2016 | DaCosta |
| D766,434 S | 9/2016 | DaCosta |
| D766,437 S | 9/2016 | DaCosta |
| D766,438 S | 9/2016 | DaCosta |
| D766,439 S | 9/2016 | DaCosta |
| 9,433,452 B2 | 9/2016 | Weiner et al. |
| 9,439,767 B2 | 9/2016 | Bojarski et al. |
| 9,452,050 B2 | 9/2016 | Miles et al. |
| 9,452,057 B2 | 9/2016 | Dacosta et al. |
| 9,456,902 B2 | 10/2016 | Hacking et al. |
| 9,492,182 B2 | 11/2016 | Keefer |
| 9,498,234 B2 | 11/2016 | Goldstein et al. |
| 9,522,023 B2 | 11/2016 | Haddad et al. |
| 9,579,110 B2 | 2/2017 | Aram et al. |
| 9,579,112 B2 | 2/2017 | Catanzarite et al. |
| 9,592,084 B2 | 3/2017 | Grant |
| 9,615,834 B2 | 4/2017 | Agnihotri et al. |
| 9,622,805 B2 | 4/2017 | Santrock et al. |
| 9,622,820 B2 | 4/2017 | Baloch et al. |
| 9,662,127 B2 | 5/2017 | Meridew et al. |
| 9,668,747 B2 | 6/2017 | Metzger et al. |
| 9,687,250 B2 | 6/2017 | Dayton et al. |
| 9,707,044 B2 | 7/2017 | Davison et al. |
| 9,717,508 B2 | 8/2017 | Iannotti et al. |
| 9,737,367 B2 | 8/2017 | Steines et al. |
| 9,743,935 B2 | 8/2017 | Smith et al. |

(56) References Cited

U.S. PATENT DOCUMENTS

| | | |
|---|---|---|
| 9,750,538 B2 | 9/2017 | Soffiatti et al. |
| 9,785,747 B2 | 10/2017 | Geebelen |
| 9,786,022 B2 | 10/2017 | Park |
| 9,795,394 B2 | 10/2017 | Bonutti |
| 9,814,474 B2 | 11/2017 | Montoya et al. |
| 9,872,773 B2 | 1/2018 | Lang et al. |
| 9,888,931 B2 | 2/2018 | Bake |
| 9,907,561 B2 | 3/2018 | Luna et al. |
| 9,918,769 B2 | 3/2018 | Provencher et al. |
| 9,924,950 B2 | 3/2018 | Couture et al. |
| 9,980,760 B2 | 5/2018 | Dacosta et al. |
| 9,993,256 B2 | 6/2018 | Lipman et al. |
| 10,002,227 B2 | 6/2018 | Netravali et al. |
| 10,010,431 B2 | 7/2018 | Eraly et al. |
| 10,022,170 B2 | 7/2018 | Leemrijse et al. |
| 10,028,750 B2 | 7/2018 | Rose |
| 10,045,807 B2 | 8/2018 | Santrock et al. |
| 10,052,114 B2 | 8/2018 | Keppler et al. |
| 10,055,536 B2 | 8/2018 | Maes et al. |
| 10,064,631 B2 | 9/2018 | Dacosta et al. |
| 10,089,413 B2 | 10/2018 | Wirx-Speetjens et al. |
| 10,123,807 B2 | 11/2018 | Geebelen |
| 10,149,722 B2 | 12/2018 | Aram et al. |
| 10,159,499 B2 | 12/2018 | Dacosta et al. |
| 10,182,832 B1 | 1/2019 | Saltzman et al. |
| 10,201,357 B2 | 2/2019 | Aram et al. |
| 10,206,692 B2 | 2/2019 | Sanders |
| 10,231,745 B2 | 3/2019 | Geebelen et al. |
| 10,262,084 B2 | 4/2019 | Lavallee et al. |
| 10,265,080 B2 | 4/2019 | Hughes et al. |
| 10,282,488 B2 | 5/2019 | Eash |
| 10,292,713 B2 | 5/2019 | Fallin et al. |
| 10,327,785 B2 | 6/2019 | Bake et al. |
| 10,327,829 B2 | 6/2019 | Dacosta et al. |
| 10,342,590 B2 | 7/2019 | Barry et al. |
| 10,357,261 B2 | 7/2019 | Kugler et al. |
| 10,363,052 B2 | 7/2019 | Park et al. |
| 10,376,268 B2 | 8/2019 | Fallin et al. |
| 10,398,510 B2 | 9/2019 | Goto |
| 10,467,356 B2 | 11/2019 | Davison et al. |
| 10,470,779 B2 | 11/2019 | Fallin et al. |
| 10,512,470 B1 | 12/2019 | Bays et al. |
| 10,524,808 B1 | 1/2020 | Hissong et al. |
| 10,548,668 B2 | 2/2020 | Furrer et al. |
| 10,561,426 B1 | 2/2020 | Dayton |
| 10,575,862 B2 | 3/2020 | Bays et al. |
| 10,603,046 B2 | 3/2020 | Dayton et al. |
| 10,610,241 B2 | 4/2020 | Wagner et al. |
| 10,675,063 B2 | 6/2020 | Pavlovskaia et al. |
| 10,779,867 B2 | 9/2020 | Penzimer et al. |
| 10,779,890 B2 | 9/2020 | Weir |
| 10,786,291 B2 | 9/2020 | Weiner et al. |
| 10,828,046 B2 | 11/2020 | Rose et al. |
| 10,849,631 B2 | 12/2020 | Hatch et al. |
| 10,849,665 B2 | 12/2020 | Singh et al. |
| 10,849,670 B2 | 12/2020 | Santrock |
| 10,856,886 B2 | 12/2020 | Dacosta et al. |
| 10,856,925 B1 | 12/2020 | Pontell |
| 10,881,416 B2 | 1/2021 | Couture et al. |
| 10,881,417 B2 | 1/2021 | Mahfouz |
| 10,888,335 B2 | 1/2021 | Dayton |
| 10,888,340 B2 | 1/2021 | Awtrey et al. |
| 10,898,211 B2 | 1/2021 | Fallin et al. |
| 10,912,571 B2 | 2/2021 | Pavlovskaia et al. |
| 10,939,922 B2 | 3/2021 | Dhillon |
| 10,939,939 B1 | 3/2021 | Gil et al. |
| 10,973,529 B2 | 4/2021 | Lavallee et al. |
| 10,987,176 B2 | 4/2021 | Poltaretskyi et al. |
| 11,000,327 B2 | 5/2021 | Schlotterback et al. |
| 11,033,333 B2 | 6/2021 | Singh et al. |
| 11,058,546 B2 | 7/2021 | Hollis et al. |
| 11,065,011 B2 | 7/2021 | Bake et al. |
| 11,074,688 B2 | 7/2021 | Chabin et al. |
| 11,090,069 B2 | 8/2021 | Park |
| 11,116,518 B2 | 9/2021 | Hafez et al. |
| 11,123,115 B2 | 9/2021 | Verstreken et al. |
| 11,129,678 B2 | 9/2021 | Haslam et al. |
| 11,147,568 B2 | 10/2021 | Fitz et al. |
| 11,154,362 B2 | 10/2021 | Kim et al. |
| 11,172,945 B1 | 11/2021 | Lian |
| 11,213,305 B2 | 1/2022 | Iannotti et al. |
| 11,213,406 B2 | 1/2022 | Rodriguez et al. |
| 11,219,526 B2 | 1/2022 | Mahfouz |
| 11,259,817 B2 | 3/2022 | Fallin et al. |
| 11,278,337 B2 | 3/2022 | Bays et al. |
| 11,278,413 B1 | 3/2022 | Lang |
| 11,304,705 B2 | 4/2022 | Fallin et al. |
| 11,426,184 B2 | 8/2022 | Rivet-Sabourin |
| 11,497,557 B2 | 11/2022 | Bojarski et al. |
| 11,633,197 B2 | 4/2023 | Denham et al. |
| 2002/0099381 A1 | 7/2002 | Maroney |
| 2002/0107519 A1 | 8/2002 | Dixon et al. |
| 2002/0165552 A1 | 11/2002 | Duffner |
| 2002/0198531 A1 | 12/2002 | Millard et al. |
| 2004/0010259 A1 | 1/2004 | Keller et al. |
| 2004/0039394 A1 | 2/2004 | Conti et al. |
| 2004/0097946 A1 | 5/2004 | Dietzel et al. |
| 2004/0138669 A1 | 7/2004 | Horn |
| 2005/0004676 A1 | 1/2005 | Schon et al. |
| 2005/0059978 A1 | 3/2005 | Sherry et al. |
| 2005/0070909 A1 | 3/2005 | Egger et al. |
| 2005/0075641 A1 | 4/2005 | Singhatat et al. |
| 2005/0101961 A1 | 5/2005 | Huebner et al. |
| 2005/0149042 A1 | 7/2005 | Metzger |
| 2005/0228389 A1 | 10/2005 | Stiernborg |
| 2005/0251147 A1 | 11/2005 | Novak |
| 2005/0267482 A1 | 12/2005 | Hyde |
| 2005/0273112 A1 | 12/2005 | McNamara |
| 2006/0129163 A1 | 6/2006 | McGuire |
| 2006/0206044 A1 | 9/2006 | Simon |
| 2006/0217733 A1 | 9/2006 | Plassky et al. |
| 2006/0229621 A1 | 10/2006 | Cadmus |
| 2006/0241607 A1 | 10/2006 | Myerson et al. |
| 2006/0241608 A1 | 10/2006 | Myerson et al. |
| 2006/0264961 A1 | 11/2006 | Murray-Brown |
| 2007/0010818 A1 | 1/2007 | Stone et al. |
| 2007/0123857 A1 | 5/2007 | Deffenbaugh et al. |
| 2007/0233138 A1 | 10/2007 | Figueroa et al. |
| 2007/0265634 A1 | 11/2007 | Weinstein |
| 2007/0276383 A1 | 11/2007 | Rayhack |
| 2008/0009863 A1 | 1/2008 | Bond et al. |
| 2008/0015603 A1 | 1/2008 | Collazo |
| 2008/0039850 A1 | 2/2008 | Rowley et al. |
| 2008/0091197 A1 | 4/2008 | Coughlin |
| 2008/0140081 A1 | 6/2008 | Heavener et al. |
| 2008/0147073 A1 | 6/2008 | Ammann et al. |
| 2008/0172054 A1 | 7/2008 | Claypool et al. |
| 2008/0195215 A1 | 8/2008 | Morton |
| 2008/0208252 A1 | 8/2008 | Holmes |
| 2008/0262500 A1 | 10/2008 | Collazo |
| 2008/0269908 A1 | 10/2008 | Warburton |
| 2008/0288004 A1 | 11/2008 | Schendel |
| 2009/0036893 A1 | 2/2009 | Kartalian et al. |
| 2009/0036931 A1 | 2/2009 | Pech et al. |
| 2009/0054899 A1 | 2/2009 | Ammann et al. |
| 2009/0087276 A1 | 4/2009 | Rose |
| 2009/0088755 A1 | 4/2009 | Aker et al. |
| 2009/0093849 A1 | 4/2009 | Grabowski |
| 2009/0105767 A1 | 4/2009 | Reiley |
| 2009/0118733 A1 | 5/2009 | Orsak et al. |
| 2009/0198244 A1 | 8/2009 | Leibel |
| 2009/0198279 A1 | 8/2009 | Zhang et al. |
| 2009/0210010 A1 | 8/2009 | Strnad et al. |
| 2009/0216089 A1 | 8/2009 | Davidson |
| 2009/0222047 A1 | 9/2009 | Graham |
| 2009/0254092 A1 | 10/2009 | Albiol Llorach |
| 2009/0254126 A1 | 10/2009 | Orbay et al. |
| 2009/0287309 A1 | 11/2009 | Walch et al. |
| 2010/0069910 A1 | 3/2010 | Hasselman |
| 2010/0121334 A1 | 5/2010 | Couture et al. |
| 2010/0130981 A1 | 5/2010 | Richards |
| 2010/0152782 A1 | 6/2010 | Stone et al. |
| 2010/0168799 A1 | 7/2010 | Schumer |
| 2010/0185245 A1 | 7/2010 | Paul et al. |

(56) References Cited

U.S. PATENT DOCUMENTS

| | | |
|---|---|---|
| 2010/0217270 A1 | 8/2010 | Polinski et al. |
| 2010/0249779 A1 | 9/2010 | Hotchkiss et al. |
| 2010/0256687 A1 | 10/2010 | Neufeld et al. |
| 2010/0318088 A1 | 12/2010 | Warne et al. |
| 2010/0324556 A1 | 12/2010 | Tyber et al. |
| 2011/0009865 A1 | 1/2011 | Orfaly |
| 2011/0093084 A1 | 4/2011 | Morton |
| 2011/0118739 A1 | 5/2011 | Tyber et al. |
| 2011/0178524 A1 | 7/2011 | Lawrence et al. |
| 2011/0213376 A1 | 9/2011 | Maxson et al. |
| 2011/0245835 A1 | 10/2011 | Dodds et al. |
| 2011/0288550 A1 | 11/2011 | Orbay et al. |
| 2011/0301648 A1 | 12/2011 | Lofthouse et al. |
| 2012/0016426 A1 | 1/2012 | Robinson |
| 2012/0065689 A1 | 3/2012 | Prasad et al. |
| 2012/0078258 A1 | 3/2012 | Lo et al. |
| 2012/0109135 A1 | 5/2012 | Bailey |
| 2012/0123420 A1 | 5/2012 | Honiball |
| 2012/0123484 A1 | 5/2012 | Lietz et al. |
| 2012/0130376 A1 | 5/2012 | Loring et al. |
| 2012/0130382 A1 | 5/2012 | Iannotti et al. |
| 2012/0130383 A1 | 5/2012 | Budoff |
| 2012/0130434 A1 | 5/2012 | Stemniski |
| 2012/0184961 A1 | 7/2012 | Johannaber |
| 2012/0185056 A1 | 7/2012 | Warburton |
| 2012/0191199 A1 | 7/2012 | Raemisch |
| 2012/0239045 A1 | 9/2012 | Li |
| 2012/0253350 A1 | 10/2012 | Anthony et al. |
| 2012/0265301 A1 | 10/2012 | Demers et al. |
| 2012/0277745 A1 | 11/2012 | Lizee |
| 2012/0303033 A1 | 11/2012 | Weiner et al. |
| 2012/0330135 A1 | 12/2012 | Millahn et al. |
| 2013/0012949 A1 | 1/2013 | Fallin et al. |
| 2013/0035694 A1 | 2/2013 | Grimm et al. |
| 2013/0085499 A1 | 4/2013 | Lian |
| 2013/0085502 A1 | 4/2013 | Harrold |
| 2013/0096563 A1 | 4/2013 | Meade et al. |
| 2013/0119579 A1 | 5/2013 | Iannotti et al. |
| 2013/0131821 A1 | 5/2013 | Cachia |
| 2013/0150900 A1 | 6/2013 | Haddad et al. |
| 2013/0150903 A1 | 6/2013 | Vincent |
| 2013/0158556 A1 | 6/2013 | Jones et al. |
| 2013/0165936 A1 | 6/2013 | Myers |
| 2013/0165938 A1 | 6/2013 | Chow et al. |
| 2013/0172942 A1 | 7/2013 | Lewis et al. |
| 2013/0184714 A1 | 7/2013 | Kaneyama et al. |
| 2013/0190765 A1 | 7/2013 | Harris et al. |
| 2013/0190766 A1 | 7/2013 | Harris et al. |
| 2013/0204259 A1 | 8/2013 | Zajac |
| 2013/0226248 A1 | 8/2013 | Hatch et al. |
| 2013/0226252 A1 | 8/2013 | Mayer |
| 2013/0231668 A1 | 9/2013 | Olsen et al. |
| 2013/0236874 A1 | 9/2013 | Iannotti et al. |
| 2013/0237987 A1 | 9/2013 | Graham |
| 2013/0237989 A1 | 9/2013 | Bonutti |
| 2013/0267956 A1 | 10/2013 | Terrill et al. |
| 2013/0292870 A1 | 11/2013 | Roger |
| 2013/0296865 A1 | 11/2013 | Aram et al. |
| 2013/0310836 A1 | 11/2013 | Raub et al. |
| 2013/0325019 A1 | 12/2013 | Thomas et al. |
| 2013/0325076 A1 | 12/2013 | Palmer et al. |
| 2013/0331845 A1 | 12/2013 | Horan et al. |
| 2013/0338785 A1 | 12/2013 | Wong |
| 2014/0005672 A1 | 1/2014 | Edwards et al. |
| 2014/0025127 A1 | 1/2014 | Richter |
| 2014/0039501 A1 | 2/2014 | Schickendantz et al. |
| 2014/0039561 A1 | 2/2014 | Weiner et al. |
| 2014/0046387 A1 | 2/2014 | Waizenegger |
| 2014/0074099 A1 | 3/2014 | Vigneron et al. |
| 2014/0074101 A1 | 3/2014 | Collazo |
| 2014/0094861 A1 | 4/2014 | Fallin |
| 2014/0094924 A1 | 4/2014 | Hacking et al. |
| 2014/0135775 A1 | 5/2014 | Maxson et al. |
| 2014/0142710 A1 | 5/2014 | Lang |
| 2014/0163563 A1 | 6/2014 | Reynolds et al. |
| 2014/0163570 A1 | 6/2014 | Reynolds et al. |
| 2014/0171953 A1 | 6/2014 | Gonzalvez et al. |
| 2014/0180342 A1 | 6/2014 | Lowery et al. |
| 2014/0188139 A1 | 7/2014 | Fallin et al. |
| 2014/0194884 A1 | 7/2014 | Martin et al. |
| 2014/0194999 A1 | 7/2014 | Orbay et al. |
| 2014/0207144 A1 | 7/2014 | Lee et al. |
| 2014/0228860 A1 | 8/2014 | Steines et al. |
| 2014/0249537 A1 | 9/2014 | Wong et al. |
| 2014/0257308 A1 | 9/2014 | Johannaber |
| 2014/0257509 A1 | 9/2014 | Dacosta et al. |
| 2014/0276815 A1 | 9/2014 | Riccione |
| 2014/0276853 A1 | 9/2014 | Long et al. |
| 2014/0277176 A1 | 9/2014 | Buchanan et al. |
| 2014/0277214 A1 | 9/2014 | Helenbolt et al. |
| 2014/0288562 A1 | 9/2014 | Von Zabern et al. |
| 2014/0296995 A1 | 10/2014 | Reiley et al. |
| 2014/0303621 A1 | 10/2014 | Gerold et al. |
| 2014/0336658 A1 | 11/2014 | Luna et al. |
| 2014/0343555 A1 | 11/2014 | Russi et al. |
| 2014/0350561 A1 | 11/2014 | Dacosta et al. |
| 2014/0371897 A1 | 12/2014 | Lin et al. |
| 2015/0032168 A1 | 1/2015 | Orsak et al. |
| 2015/0032217 A1 | 1/2015 | Bojarski et al. |
| 2015/0045801 A1 | 2/2015 | Axelson, Jr. et al. |
| 2015/0045839 A1 | 2/2015 | Dacosta et al. |
| 2015/0051650 A1 | 2/2015 | Verstreken et al. |
| 2015/0057667 A1 | 2/2015 | Ammann et al. |
| 2015/0066094 A1 | 3/2015 | Prandi et al. |
| 2015/0112446 A1 | 4/2015 | Melamed et al. |
| 2015/0119944 A1 | 4/2015 | Geldwert |
| 2015/0142000 A1 | 5/2015 | Seedhom et al. |
| 2015/0142064 A1 | 5/2015 | Perez et al. |
| 2015/0150608 A1 | 6/2015 | Sammarco |
| 2015/0182273 A1 | 7/2015 | Stemniski et al. |
| 2015/0223851 A1 | 8/2015 | Hill et al. |
| 2015/0230843 A1 | 8/2015 | Palmer et al. |
| 2015/0245858 A1 | 9/2015 | Weiner et al. |
| 2015/0305752 A1 | 10/2015 | Eash |
| 2015/0342756 A1 | 12/2015 | Bays et al. |
| 2015/0351916 A1 | 12/2015 | Kosarek et al. |
| 2016/0015426 A1 | 1/2016 | Dayton |
| 2016/0022315 A1 | 1/2016 | Soffiatti et al. |
| 2016/0135858 A1 | 5/2016 | Dacosta et al. |
| 2016/0151165 A1 | 6/2016 | Fallin et al. |
| 2016/0175089 A1 | 6/2016 | Fallin et al. |
| 2016/0192949 A1 | 7/2016 | Robichaud et al. |
| 2016/0192950 A1 | 7/2016 | Dayton et al. |
| 2016/0192951 A1 | 7/2016 | Gelaude et al. |
| 2016/0199076 A1 | 7/2016 | Fallin et al. |
| 2016/0206331 A1 | 7/2016 | Fitz et al. |
| 2016/0206379 A1 | 7/2016 | Flett et al. |
| 2016/0213384 A1 | 7/2016 | Fallin et al. |
| 2016/0235414 A1 | 8/2016 | Hatch et al. |
| 2016/0242791 A1 | 8/2016 | Fallin et al. |
| 2016/0256204 A1 | 9/2016 | Patel et al. |
| 2016/0270855 A1 | 9/2016 | Kunz et al. |
| 2016/0324532 A1 | 11/2016 | Montoya et al. |
| 2016/0324555 A1 | 11/2016 | Brumfield et al. |
| 2016/0331467 A1 | 11/2016 | Slamin et al. |
| 2016/0354127 A1 | 12/2016 | Undquist et al. |
| 2016/0361071 A1 | 12/2016 | Mahfouz |
| 2017/0000498 A1 | 1/2017 | Grant et al. |
| 2017/0007408 A1 | 1/2017 | Fitz et al. |
| 2017/0014143 A1 | 1/2017 | Dayton et al. |
| 2017/0014173 A1 | 1/2017 | Smith et al. |
| 2017/0020537 A1 | 1/2017 | Tuten |
| 2017/0027593 A1 | 2/2017 | Bojarski et al. |
| 2017/0042598 A1* | 2/2017 | Santrock ............ A61B 17/1682 |
| 2017/0042599 A1 | 2/2017 | Bays et al. |
| 2017/0056183 A1 | 3/2017 | Steines et al. |
| 2017/0065347 A1 | 3/2017 | Bojarski et al. |
| 2017/0079669 A1 | 3/2017 | Bays et al. |
| 2017/0143511 A1 | 5/2017 | Cachia |
| 2017/0164989 A1 | 6/2017 | Weiner et al. |
| 2017/0164990 A1 | 6/2017 | Weiner et al. |
| 2017/0231645 A1 | 8/2017 | Metzger et al. |
| 2017/0245906 A1 | 8/2017 | Kugler et al. |
| 2017/0245935 A1 | 8/2017 | Kugler et al. |

(56) References Cited

U.S. PATENT DOCUMENTS

| | | |
|---|---|---|
| 2017/0249440 A1 | 8/2017 | Lang et al. |
| 2017/0290614 A1 | 10/2017 | Weiner et al. |
| 2017/0360578 A1 | 12/2017 | Shin et al. |
| 2018/0021145 A1 | 1/2018 | Seavey et al. |
| 2018/0033338 A1 | 2/2018 | Iannotti et al. |
| 2018/0036019 A1 | 2/2018 | Iannotti et al. |
| 2018/0049758 A1 | 2/2018 | Amis et al. |
| 2018/0085133 A1 | 3/2018 | Lavallee et al. |
| 2018/0110530 A1 | 4/2018 | Wagner et al. |
| 2018/0116804 A1 | 5/2018 | Hafez et al. |
| 2018/0125504 A1 | 5/2018 | Dayton et al. |
| 2018/0132868 A1 | 5/2018 | Dacosta et al. |
| 2018/0146970 A1 | 5/2018 | Luna et al. |
| 2018/0185097 A1 | 7/2018 | Langhorn et al. |
| 2018/0235641 A1 | 8/2018 | McAuliffe et al. |
| 2018/0235765 A1 | 8/2018 | Welker et al. |
| 2018/0271569 A1 | 9/2018 | Verkstreken et al. |
| 2018/0289380 A1 | 10/2018 | Mauldin et al. |
| 2018/0317986 A1 | 11/2018 | Jackman et al. |
| 2018/0317992 A1 | 11/2018 | Antrock et al. |
| 2018/0344326 A1 | 12/2018 | Chan et al. |
| 2018/0344334 A1 | 12/2018 | Kim et al. |
| 2018/0344409 A1 | 12/2018 | Bonny et al. |
| 2019/0000629 A1 | 1/2019 | Winslow |
| 2019/0008532 A1 | 1/2019 | Fitz et al. |
| 2019/0015113 A1 | 1/2019 | Morvan |
| 2019/0059913 A1 | 2/2019 | Saltzman et al. |
| 2019/0099189 A1 | 4/2019 | Fallin et al. |
| 2019/0117286 A1 | 4/2019 | Tyber et al. |
| 2019/0146458 A1 | 5/2019 | Roh et al. |
| 2019/0175237 A1 | 6/2019 | Treace et al. |
| 2019/0254681 A1 | 8/2019 | Couture et al. |
| 2019/0274745 A1 | 9/2019 | Smith et al. |
| 2019/0282302 A1 | 9/2019 | Park |
| 2019/0307495 A1 | 10/2019 | Geldwert |
| 2019/0328435 A1 | 10/2019 | Bays et al. |
| 2019/0328436 A1 | 10/2019 | Bays et al. |
| 2019/0336140 A1 | 11/2019 | Dacosta et al. |
| 2019/0350602 A1 | 11/2019 | Stemniski et al. |
| 2019/0357919 A1 | 11/2019 | Fallin et al. |
| 2019/0365419 A1 | 12/2019 | Rhodes et al. |
| 2019/0374237 A1 | 12/2019 | Metzger et al. |
| 2019/0388240 A1 | 12/2019 | Courtis et al. |
| 2020/0015856 A1 | 1/2020 | Treace et al. |
| 2020/0015874 A1 | 1/2020 | Hartson et al. |
| 2020/0046374 A1 | 2/2020 | Luttrell et al. |
| 2020/0054351 A1 | 2/2020 | Meridew et al. |
| 2020/0060739 A1 | 2/2020 | Nachtrab et al. |
| 2020/0085452 A1 | 3/2020 | Siegler |
| 2020/0085588 A1 | 3/2020 | Mauldin et al. |
| 2020/0129213 A1 | 4/2020 | Singh et al. |
| 2020/0155176 A1 | 5/2020 | Bays et al. |
| 2020/0188134 A1 | 6/2020 | Mullen et al. |
| 2020/0237386 A1 | 7/2020 | Stemniski et al. |
| 2020/0246027 A1 | 8/2020 | Robichaud et al. |
| 2020/0253641 A1 | 8/2020 | Treace et al. |
| 2020/0253740 A1 | 8/2020 | Puncreobutr et al. |
| 2020/0258227 A1 | 8/2020 | Liao et al. |
| 2020/0297495 A1 | 9/2020 | Gemon et al. |
| 2020/0315708 A1 | 10/2020 | Mosnier et al. |
| 2020/0334871 A1 | 10/2020 | Su et al. |
| 2020/0349699 A1 | 11/2020 | Shah |
| 2020/0352580 A1 | 11/2020 | Saltzman et al. |
| 2020/0352582 A1 | 11/2020 | Larche et al. |
| 2020/0390452 A1 | 12/2020 | Bojarski et al. |
| 2021/0015527 A1 | 1/2021 | Singh et al. |
| 2021/0038212 A1 | 2/2021 | May et al. |
| 2021/0042458 A1 | 2/2021 | Dayal et al. |
| 2021/0059691 A1 | 3/2021 | Zille |
| 2021/0068846 A1 | 3/2021 | Langhorn et al. |
| 2021/0077131 A1 | 3/2021 | Denham et al. |
| 2021/0077192 A1 | 3/2021 | Perler et al. |
| 2021/0090248 A1 | 3/2021 | Choi et al. |
| 2021/0093328 A1 | 4/2021 | Dayton et al. |
| 2021/0093365 A1 | 4/2021 | Dayton et al. |
| 2021/0106372 A1 | 4/2021 | Tyber et al. |
| 2021/0113222 A1 | 4/2021 | Khatibi et al. |
| 2021/0121297 A1 | 4/2021 | Cavanagh et al. |
| 2021/0137613 A1 | 5/2021 | Chi |
| 2021/0145456 A1 | 5/2021 | Dhillon |
| 2021/0145461 A1 | 5/2021 | McGinley et al. |
| 2021/0145518 A1 | 5/2021 | Mosnier et al. |
| 2021/0153948 A1 | 5/2021 | Stifter et al. |
| 2021/0161543 A1 | 6/2021 | McAuliffe et al. |
| 2021/0186704 A1 | 6/2021 | Fitz et al. |
| 2021/0196290 A1 | 7/2021 | Annotti et al. |
| 2021/0205099 A1 | 7/2021 | Parr |
| 2021/0210189 A1 | 7/2021 | Casey et al. |
| 2021/0212705 A1 | 7/2021 | Reynolds et al. |
| 2021/0244477 A1 | 8/2021 | Singh et al. |
| 2021/0251670 A1 | 8/2021 | Sayger et al. |
| 2021/0259713 A1 | 8/2021 | Trabish et al. |
| 2021/0267730 A1 | 9/2021 | Azernikov et al. |
| 2021/0272134 A1 | 9/2021 | Indani et al. |
| 2021/0275196 A1 | 9/2021 | Wodajo |
| 2021/0282790 A1 | 9/2021 | Sellman et al. |
| 2021/0290319 A1 | 9/2021 | Poltaretskyi et al. |
| 2021/0307796 A1 | 10/2021 | Marien et al. |
| 2021/0307833 A1 | 10/2021 | Farley et al. |
| 2021/0315593 A1 | 10/2021 | Mauldin et al. |
| 2021/0322034 A1 | 10/2021 | Athwal et al. |
| 2021/0330311 A1 | 10/2021 | Denham et al. |
| 2021/0330336 A1 | 10/2021 | Courtis et al. |
| 2021/0330339 A1 | 10/2021 | Robichaud |
| 2021/0330468 A1 | 10/2021 | Mimnaugh et al. |
| 2021/0338450 A1 | 11/2021 | Hollis et al. |
| 2021/0346091 A1 | 11/2021 | Haslam et al. |
| 2021/0353304 A1 | 11/2021 | Robichaud |
| 2021/0353312 A1 | 11/2021 | Robichaud |
| 2021/0361297 A1 | 11/2021 | Luna et al. |
| 2021/0361300 A1 | 11/2021 | McGinley et al. |
| 2021/0361330 A1 | 11/2021 | McAleer et al. |
| 2021/0361437 A1 | 11/2021 | Lang et al. |
| 2021/0369289 A1 | 12/2021 | Lee |
| 2021/0369305 A1 | 12/2021 | Rhodes et al. |
| 2021/0378687 A1 | 12/2021 | McGinley et al. |
| 2021/0378752 A1 | 12/2021 | Paul et al. |
| 2021/0391058 A1 | 12/2021 | Kostrzewski et al. |
| 2021/0393304 A1 | 12/2021 | Geldwert |
| 2022/0000556 A1 | 1/2022 | Casey et al. |
| 2022/0008085 A1 | 1/2022 | Carroll et al. |
| 2022/0015861 A1 | 1/2022 | Basta |
| 2022/0022894 A1 | 1/2022 | Allard et al. |
| 2022/0031396 A1 | 2/2022 | Ryan et al. |
| 2022/0031475 A1 | 2/2022 | Deransart et al. |
| 2022/0079645 A1 | 3/2022 | Smith et al. |
| 2022/0079678 A1 | 3/2022 | Mckinnon et al. |
| 2022/0084651 A1 | 3/2022 | Farley et al. |
| 2022/0087822 A1 | 3/2022 | Radermacher et al. |
| 2022/0087827 A1 | 3/2022 | Bojarski et al. |
| 2022/0160430 A1 | 5/2022 | Landon et al. |

FOREIGN PATENT DOCUMENTS

| | | |
|---|---|---|
| AU | 2020220169 B2 | 9/2021 |
| AU | 2021286392 A1 | 1/2022 |
| CN | 105105853 B | 12/2015 |
| CN | 106236185 A | 12/2016 |
| CN | 205924106 | 2/2017 |
| CN | 206151532 | 5/2017 |
| CN | 108030532 A | 5/2018 |
| CN | 207721902 | 8/2018 |
| CN | 112914724 B | 6/2021 |
| DE | 2910627 A1 | 9/1980 |
| EP | 0097001 A1 | 12/1983 |
| EP | 2844162 A2 | 3/2015 |
| EP | 2856951 A1 | 4/2015 |
| EP | 2685914 B1 | 9/2015 |
| EP | 3000443 A3 | 7/2016 |
| EP | 2400900 B1 | 12/2016 |
| EP | 2713921 B1 | 10/2017 |
| EP | 2083758 B1 | 11/2017 |
| EP | 3384865 A1 | 10/2018 |
| EP | 3013256 B1 | 11/2018 |

(56) References Cited

FOREIGN PATENT DOCUMENTS

| | | | |
|---|---|---|---|
| EP | 3171795 B1 | 11/2018 | |
| EP | 3672535 A1 | 7/2020 | |
| EP | 3307182 | 11/2020 | |
| EP | 3740141 | 11/2020 | |
| EP | 2558010 | 5/2021 | |
| EP | 3948895 | 2/2022 | |
| GB | 202014536 | 10/2020 | |
| KR | 101952368 B1 | 2/2019 | |
| RU | 182499 | 8/2018 | |
| WO | 2009045960 A1 | 4/2009 | |
| WO | 2009105196 A1 | 8/2009 | |
| WO | WO2012024317 A2 | 2/2012 | |
| WO | WO 2012/088036 | 6/2012 | |
| WO | WO2012176077 A1 | 12/2012 | |
| WO | WO2013041618 A1 | 3/2013 | |
| WO | WO2013156816 A2 | 10/2013 | |
| WO | 2014154266 A1 | 10/2014 | |
| WO | WO2015003284 A2 | 1/2015 | |
| WO | 2015003284 A3 | 4/2015 | |
| WO | WO2016/012731 A1 | 1/2016 | |
| WO | WO2016102025 A1 | 6/2016 | |
| WO | WO 2017/031000 | 2/2017 | |
| WO | WO2018167369 A1 | 9/2018 | |
| WO | WO2019052622 | 3/2019 | |
| WO | WO2019060780 A2 | 3/2019 | |
| WO | 2019091537 A1 | 5/2019 | |
| WO | WO2020239909 | 2/2021 | |
| WO | WO2021028636 | 4/2021 | |
| WO | WO2021118733 A1 | 6/2021 | |
| WO | WO2021236838 A1 | 11/2021 | |
| WO | WO2021240290 A1 | 12/2021 | |
| WO | WO2022033648 A1 | 2/2022 | |
| ZA | 201003003 B | 12/1899 | |

OTHER PUBLICATIONS

Dubovik et al., "Talonavicular joint arthrodesis and medial displacement calcaneal osteotomy for treatment of patients with planovalgus deformity", *Traumatology and Orthopedics of Russia*, 2012:3(65), 83-88 (English Abstract Only).
Additive Orthopaedics, "The First and Only FDA Approved Patient Specific Talus Spacer", 2021, 11 pgs https://totaltalusreplacement.com/.
Treace Medical Concepts, Inc. "Adductoplasty Midfoot Correction System" 2022, 9 pgs. https://www.lapiplasty.com/surgeons/other-products/adductoplasty-system/.
Nyska, Synergy 3D Med "Anatomical Model: Calcaneus", 2022.
Total Ankle Institute, "Prophecy: Preoperative Navigation Guides", 2019, 6 pgs https://www.totalankleinstitute.com/infinity-products/prophecy-preoperative-navigation-guides/.
Arthrex, Distal Tibia Allograft Workstation for Glenoid Bone Loss, Surgical Technique, 2018, 8 pgs.
De Carvalho et al., "Automated three-dimensional distance and coverage mapping of hallux valgus: a case-control study", J Foot Ankle. 2022;16(1):41-45 https://jfootankle.com/JournalFootAnkle/article/view/1629/1821 retrieved May 26, 2022.
Wright Med, "How Blueprint Works—from CT to 3D [CAW-9389]", 2021 https://www.wrightmeded.com/videos/how-blueprint-works-from-ct-to-3d-caw-9389 (submit video?)—video teaches auto segmentation. Video at top of this page at time mark 00:32 seconds to time mark 00:48.
Tornier Technology, "Tornier Blueprint 3D Planning + PSI", Feb. 2017, 12 pgs. https://www.wrightemedia.com/ProductFiles/Files/PDFs/CAW-8609_EN_HR_LE.pdf.
Synopsys, Simpleware Automated Solution Modules, "Medical Image Segmentation with Machine Learning" 2022, 12 pgs https://www.synopsys.com/simpleware/software/auto-segmenter-modules.html#simpleware-as-ortho.
Virzi, et al. "Comprehensive Review of 3D Segmentation Software Tools for MRI Usable for Pelvic Surgery Planning." Journal of digital imaging vol. 33,1 (2020): 99-110. doi:10.1007/s10278-019-00239-7.
Disior, "Bonelogic foot & ankle module", 2022, 6pgs. https://www.disior.com/foot--ankle.html.
KLS Martin Group, IPS Implants, 2022, 8 pgs. https://www.klsmartin.com/en-na/products/individual-patient-solutions/ips-implants/.
Aiyer et al., "Prevalence of Metatarsus Adductus in Patients Undergoing Hallux Valgus Surgery," Foot & Ankle International, vol. 35, No. 12, 2014, pp. 1292-1297.
Bennett et al., "Intraosseous Sliding Plate Fixation Used in Double Osteotomy Bunionectomy," Foot & Ankle International, vol. 40, No. 1, 2019, pp. 85-88.
Buda et al., "Effect of Fixation Type and Bone Graft on Tarsometatarsal Fusion," Foot & Ankle International, vol. 39, No. 12, 2018, pp. 1394-1402.
Chomej et al., "Lateralising Dmmo (Mis) for simultaneous correction of a pes adductus during surgical treatment of a hallux valgus," The Foot, vol. 45, Dec. 2020, 33 pages.
Cichero et al., "Different fixation constructs and the risk of non-union following first metatarsophalangeal joint arthrodesis," Foot and Ankle Surgery, vol. 27, 2021, pp. 789-792.
Curran et al., "Functional Capabilities After First Metatarsal Phalangeal Joint Arthrodesis Using a Locking Plate and Compression Screw Construct," The Journal of Foot & Ankle Surgery, vol. 61, No. 1, Jan./Feb. 2022, pp. 79-83.
Dalat et al., "Does arthrodesis of the first metatarsophalangeal joint correct the intermetatarsal M1M2 angle? Analysis of a continuous series of 208 arthrodeses fixed with plates," Orthopaedics & Traumatology: Surgery & Research, vol. 101, 2015, pp. 709-714.
Deheer et al., "Procedure-Specific Hardware Removal After Evans Osteotomy," Journal of the American Podiatric Medical Association, vol. 110, No. 2, Mar./Apr. 2020, 7 pages.
Fazal et al., "First metatarsophalangeal joint arthrodesis with two orthogonal two hole plates," Acta Orthopaedica et Traumatologica Turcica, vol. 52, 2018, pp. 363-366.
Ferreyra et al., "Can we correct first metatarsal rotation and sesamoid position with the 3D Lapidus procedure?," Foot and Ankle Surgery, vol. 28, No. 3, Apr. 2022, pp. 313-318.
Flavin et al., "Arthrodesis of the First Metatarsophalangeal Joint Using a Dorsal Titanium Contoured Plate," Foot & Ankle International, vol. 25, No. 11, Nov. 2004, pp. 783-787.
Fraissler et al., "Treatment of hallux valgus deformity," Efort Open Reviews, vol. 1, Aug. 2016, pp. 295-302.
Gould et al., "A Prospective Evaluation of First Metatarsophalangeal Fusion Using an Innovative Dorsal Compression Plating System," The Journal of Foot & Ankle Surgery, vol. 60, 2021, pp. 891-896.
Gutteck et al., "Comparative study of Lapidus bunionectomy using different osteosynthesis methods," Foot and Ankle Surgery, vol. 19, 2013, pp. 218-221.
Gutteck et al., "Is it feasible to rely on intraoperative X ray in correcting hallux valgus?," Archives of Orthopaedic and Trauma Surgery, vol. 133, 2013, pp. 753-755.
Ho et al., "Hallux rigidus," Efort Open Reviews, vol. 2, Jan. 2017, pp. 13-20.
Hunt et al., "Locked Versus Nonlocked Plate Fixation For Hallux MTP Arthrodesis," Foot and Ankle International, vol. 32, No. 7, Jul. 2011, pp. 704-709.
Jackson III et al., "The Surgical Learning Curve for Modified Lapidus Procedure for Hallux Valgus Deformity," Foot & Ankle Specialist, Jul. 2021, 5 pages.
Jeuken et al., "Long-term Follow-up of a Randomized Controlled Trial Comparing Scarf to Chevron Osteotomy in Hallux Valgus Correction," Foot & Ankle International, vol. 37, No. 7, 2016, pp. 687-695.
Klos et al., "Modified Lapidus arthrodesis with plantar plate and compression screw for treatment of hallux valgus with hypermobility of the first ray: A preliminary report," Foot and Ankle Surgery, vol. 19, 2013, pp. 239-244.
Kurup et al., "Midfoot arthritis- current concepts review," Journal of Clinical Orthopaedics and Trauma, vol. 11, 2020, pp. 399-405.
La Reaux et al., "Metatarsus adductus and hallux abducto valgus: their correlation," The Journal of Foot Surgery, vol. 26, No. 4, Jul. 1987, pp. 304-308, Abstract Only.

(56) References Cited

OTHER PUBLICATIONS

Latif et al., "First metatarsophalangeal fusion using joint specific dorsal plate with interfragmentary screw augmentation: Clinical and radiological outcomes," Foot and Ankle Surgery, vol. 25, 2019, pp. 132-136.
Little, "Joint Arthrodesis For Hallux Valgus," Clinics in Podiatric Medicine and Surgery, Hallux Abducto Valgus Surgery, updated Apr. 19, 2014, retrieved online from <https://www.footankleinstitute.com/first-metatarsophalangeal-joint-arthrodesis-in-the-treatment-of-hallux-valgus>, 7 pages.
Machacek Jr et al., "Salvage of a Failed Keller Resection Arthroplasty," The Journal of Bone and Joint Surgery, vol. 36A, No. 6, Jun. 2004, pp. 1131-1138.
Marshall et al., "The identification and appraisal of assessment tools used to evaluate metatarsus adductus: a systematic review of their measurement properties," Journal of Foot and Ankle Research, vol. 11, No. 25, 2018, 10 pages.
McAleer et al., "Radiographic Outcomes Following Triplanar Correction of Combined Hallux Valgus and Metatarsus Adductus Deformities," ACFAS Scientific Conference, Poster, Feb. 2022, 1 page.
McCabe et al., "Anatomical reconstruction of first ray instability hallux valgus with a medial anatomical TMTJ1 plate," Foot and Ankle Surgery, vol. 27, No. 8, Dec. 2021, pp. 869-873.
Mehtar et al., "Outcomes of bilateral simultaneous hallux MTPJ fusion," Foot and Ankle Surgery, vol. 27, 2021, pp. 213-216.
Miller et al., "Variable Angle Locking Compression Plate as Alternative Fixation for Jones Fractures: A Case Series," Kansas Journal of Medicine, vol. 12, No. 2, May 2019, pp. 28-32.
Nix et al., "Prevalence of hallux valgus in the general population: a systematic review and meta-analysis," Journal of Foot and Ankle Research, vol. 3, No. 21, 2010, 9 pages.
Park et al., "Comparative analysis of clinical outcomes of fixed-angle versus variable-angle locking compression plate for the treatment of Lisfranc injuries," Foot and Ankle Surgery, vol. 26, 2020, pp. 338-342.
Pentikainen et al., "Preoperative Radiological Factors Correlated to Long-Term Recurrence of Hallux Valgus Following Distal Chevron Osteotomy," Foot & Ankle International, vol. 35, No. 12, 2014, pp. 1262-1267.
Shima et al., "Operative Treatment for Hallux Valgus With Moderate to Severe Metatarsus Adductus," Foot & Ankle International, vol. 40, No. 6, 2019, pp. 641-647.
Simons et al., "Short-Term Clinical Outcome of Hemiarthroplasty Versus Arthrodesis for End-Stage Hallux Rigidus," The Journal of Foot & Ankle Surgery, vol. 54, 2015, pp. 848-851.
Weigelt et al., "Risk Factors for Nonunion After First Metatarsophalangeal Joint Arthrodesis With a Dorsal Locking Plate and Compression Screw Construct: Correction of Hallux Valgus Is Key," The Journal of Foot & Ankle Surgery, vol. 60, No. 6, Nov./Dec. 2021, pp. 1179-1183.
Williams et al., "Metatarsus adductus: Development of a nonsurgical treatment pathway," Journal of Paediatrics and Child Health, vol. 49, 2013, pp. E428-433.
Hatch et al., "Analysis of Shortening and Elevation of the First Ray With Instrumented Triplane First Tarsometatarsal Arthrodesis," Foot & Ankle Orthopaedics, vol. 5, No. 4, 2020, pp. 1-8.
Ray et al., "Hallux Valgus," Foot & Ankle Orthopaedics, vol. 4, No. 2, 2019, pp. 1-12.
Santrock et al., "Hallux Valgus Deformity and Treatment: A Three-Dimensional Approach: Lapiplasty," Foot & Ankle Clinics, vol. 23, No. 2, 2018, pp. 281-295.
International Patent Application No. PCT/US2021/033256, International Search Report and Written Opinion dated Sep. 7, 2021, 9 pages.
Smith et al., "Intraoperative Multiplanar Alignment System to Guide Triplanar Correction of Hallux Valgus Deformity," Techniques in Foot & Ankle Surgery, 2017, 8 pages.

Smith et al., "Understanding Frontal Plane Correction in Hallux Valgus Repair," Clinics in Podiatric Medicine and Surgery, vol. 35, 2018, pp. 27-36.
DiNapoli et al., "Metatarsal Osteotomy for the Correction of Metatarsus Adductus," Reconstructive Surgery of the Foot and Leg, 1989, pp. 242-250.
McAleer et al., "A systematic approach to the surgical correction of combined hallux valgus and metatarsus adductus deformities," The Journal of Foot & Ankle Surgery, May 21, 2021, 6 pages.
Dayton et al., "Dorsal Suspension Stitch: An Alternative Stabilization After Flexor Tenotomy for Flexible Hammer Digit Syndrome," The Journal of Foot and Ankle Surgery, vol. 48, No. 5, Sep./Oct. 2009, pp. 602-605.
Dayton et al., "The Extended Knee Hemilithotomy Position for Gastrocnemius Recession," The Journal of Foot and Ankle Surgery, vol. 49, 2010, pp. 214-216.
Wienke et al., "Bone Stimulation For Nonunions: What the Evidence Reveals," Podiatry Today, vol. 24, No. 9, Sep. 2011, pp. 52-57.
Dayton et al., "Hallux Varus as Complication of Foot Compartment Syndrome," The Journal of Foot and Ankle Surgery, vol. 50, 2011, pp. 504-506.
Dayton et al., "Measurement of Mid-Calcaneal Length on Plain Radiographs: Reliability of a New Method," Foot and Ankle Specialist, vol. 4, No. 5, Oct. 2011, pp. 280-283.
Dayton et al., "A User-Friendly Method of Pin Site Management for External Fixators," Foot and Ankle Specialist, Sep. 16, 2011, 4 pages.
Dayton et al., "Effectiveness of a Locking Plate in Preserving Midcalcaneal Length and Positional Outcome after Evans Calcaneal Osteotomy: A Retrospective Pilot Study," The Journal of Foot and Ankle Surgery, vol. 52, 2013, pp. 710-713.
Dayton et al., "Does Postoperative Showering or Bathing of a Surgical Site Increase the Incidence of Infection? A Systematic Review of the Literature," The Journal of Foot and Ankle Surgery, vol. 52, 2013, pp. 612-614.
Dayton et al., "Technique for Minimally Invasive Reduction of Calcaneal Fractures Using Small Bilateral External Fixation," The Journal of Foot and Ankle Surgery, Article in Press, 2014, 7 pages.
Dayton et al., "Clarification of the Anatomic Definition of the Bunion Deformity," The Journal of Foot and Ankle Surgery, vol. 53, 2014, pp. 160-163.
Dayton et al., "Observed Changes in Radiographic Measurements of the First Ray after Frontal Plane Rotation of the First Metatarsal in a Cadaveric Foot Model," The Journal of Foot and Ankle Surgery, Article in Press, 2014, 5 pages.
Dayton et al., "Observed Changes in First Metatarsal and Medial Cuneiform Positions after First Metatarsophalangeal Joint Arthrodesis," The Journal of Foot and Ankle Surgery, vol. 53, 2014, pp. 32-35.
Dayton et al., "Reduction of the Intermetatarsal Angle after First Metatarsal Phalangeal Joint Arthrodesis: A Systematic Review," The Journal of Foot and Ankle Surgery, Article in Press, 2014, 4 pages.
Feilmeier et al., "Reduction of Intermetatarsal Angle after First Metatarsophalangeal Joint Arthrodesis in Patients with Hallux Valgus," The Journal of Foot and Ankle Surgery, vol. 53, 2014, pp. 29-31.
Dayton et al., "Principles of Management of Growth Plate Fractures in the Foot and Ankle," Clinics in Podiatric Medicine and Surgery, Pediatric Foot Deformities, Oct. 2013, 17 pages.
Dayton et al., "Observed Changes in Radiographic Measurements of the First Ray after Frontal and Transverse Plane Rotation of the Hallux: Does the Hallux Drive the Metatarsal in a Bunion Deformity?," The Journal of Foot and Ankle Surgery, Article in Press, 2014, 4 pages.
Rodriguez et al., "Ilizarov method of fixation for the management of pilon and distal tibial fractures in the compromised diabetic patient: A technique guide," The Foot and Ankle Journal Online, vol. 7, No. 2, 2014, 9 pages.
Feilmeier et al., "Incidence of Surgical Site Infection in the Foot and Ankle with Early Exposure and Showering of Surgical Sites: A Prospective Observation," The Journal of Foot and Ankle Surgery, vol. 53, 2014, pp. 173-175.

(56) References Cited

OTHER PUBLICATIONS

Catanese et al., "Measuring Sesamoid Position in Hallux Valgus: When Is the Sesamoid Axial View Necessary," Foot and Ankle Specialist, 2014, 3 pages.
Dayton et al., "Comparison of Complications for Internal and External Fixation for Charcot Reconstruction: A Systematic Review," The Journal of Foot and Ankle Surgery, Article in Press, 2015, 4 pages.
Dayton et al., "A new triplanar paradigm for bunion management," Lower Extremity Review, Apr. 2015, 9 pages.
Dayton et al., "American College of Foot and Ankle Surgeons' Clinical Consensus Statement: Perioperative Prophylactic Antibiotic Use in Clean Elective Foot Surgery," The Journal of Foot and Ankle Surgery, Article in Press, 2015, 7 pages.
Dayton et al., "Complications of Metatarsal Suture Techniques for Bunion Correction: A Systematic Review of the Literature," The Journal of Foot and Ankle Surgery, Article in Press, 2015, 3 pages.
DeCarbo et al., "The Weil Osteotomy: A Refresher," Techniques in Foot and Ankle Surgery, vol. 13, No. 4, Dec. 2014, pp. 191-198.
DeCarbo et al., "Resurfacing Interpositional Arthroplasty for Degenerative Joint Diseas of the First Metatarsalphalangeal Joint," Podiatry Management, Jan. 2013, pp. 137-142.
DeCarbo et al., "Locking Plates: Do They Prevent Complications?," Podiatry Today, Apr. 2014, 7 pages.
Easley et al., "Current Concepts Review: Hallux Valgus Part II: Operative Treatment," Foot and Ankle International, vol. 28, No. 6, Jun. 2007, pp. 748-758.
Kim et al., "A Multicenter Retrospective Review of Outcomes for Arthrodesis, Hemi-Metallic Joint Implant, and Resectional Arthroplasty in the Surgical Treatment of End-Stage Hallux Rigidus," The Journal of Foot and Ankle Surgery, vol. 51, 2012, pp. 50-56.
Easley et al., "Current Concepts Review: Hallux Valgus Part I: Pathomechanics, Clinical Assessment, and Nonoperative Management," Foot and Ankle International, vol. 28, No. 5, May 2007, pp. 654-659.
Sandhu et al., "Digital Arthrodesis With a One-Piece Memory Nitinol Intramedullary Fixation Device: A Retrospective Review," Foot and Ankle Specialist, vol. 6, No. 5, Oct. 2013, pp. 364-366.
Weber et al., "Use of the First Ray Splay Test to Assess Transverse Plane Instability Before First Metatarsocuneiform Fusion," The Journal of Foot and Ankle Surgery, vol. 45, No. 4, Jul./Aug. 2006, pp. 278-282.
Smith et al., "Opening Wedge Osteotomies for Correction of Hallux Valgus: A Review of Wedge Plate Fixation," Foot and Ankle Specialist, vol. 2, No. 6, Dec. 2009, pp. 277-282.
Easley et al., "What is the Best Treatment for Hallux Valgus?," Evidence-Based Orthopaedics—The Best Answers to Clinical Questions, Chapter 73, 2009, pp. 479-491.
Shurnas et al., "Proximal Metatarsal Opening Wedge Osteotomy," Operative Techniques in Foot and Ankle Surgery, Section I, Chapter 13, 2011, pp. 73-78.
Coetzee et al., "Revision Hallux Valgus Correction," Operative Techniques in Foot and Ankle Surgery, Section I, Chapter 15, 2011, pp. 84-96.
E et al., "Tarsometatarsal Arthrodesis," Operative Techniques in Foot and Ankle Surgery, Section II, Chapter 40, 2011, pp. 281-285.
Collan et al., "The biomechanics of the first metatarsal bone in hallux valgus: A preliminary study utilizing a weight bearing extremity CT," Foot and Ankle Surgery, vol. 19, 2013, pp. 155-161.
Eustace et al., "Hallux valgus, first metatarsal pronation and collapse of the medial longitudinal arch - a radiological correlation," Skeletal Radiology, vol. 23, 1994, pp. 191-194.
Mizuno et al., "Detorsion Osteotomy of the First Metatarsal Bone in Hallux Valgus," Japanese Orthopaedic Association, Tokyo, 1956; 30:813-819.
Okuda et al., "The Shape of the Lateral Edge of the First Metatarsal Head as a Risk Factor for Recurrence of Hallux Valgus," The Journal of Bone and Joint Surgery, vol. 89, 2007, pp. 2163-2172.
Okuda et al., "Proximal Metatarsal Osteotomy for Hallux Valgus: Comparison of Outcome for Moderate and Severe Deformities," Foot and Ankle International, vol. 29, No. 7, Jul. 2008, pp. 664-670.
D'AMICO et al., "Motion of the First Ray: Clarification Through Investigation," Journal of the American Podiatry Association, vol. 69, No. 1, Jan. 1979, pp. 17-23.
Groves, "Operative Report," St. Tammany Parish Hospital, Date of Procedure, Mar. 26, 2014, 2 pages.
Claim Chart for Groves Public Use (Mar. 26, 2014), Exhibit B4 of Defendant Fusion Orthopedics LLC's Invalidity Contentions, No. CV-22-00490-PHX-SRB, US District Court for the District of Arizona, Aug. 27, 2022, 161 pages.
Crawford et al., "Metatarsus Adductus: Radiographic and Pathomechanical Analysis," Chapter 5, 2014, 6 pages.
Chesser et al., "New Advances With The Tarsometatarsal Arthrodesis," Podiatry Today, vol. 30, No. 10, Sep. 27, 2017, 15 pages.
Ferrari et al., "A Radiographic Study of the Relationship Between Metatarsus Adductus and Hallux Valgus," The Journal of Foot and Ankle Surgery, vol. 42, No. 1, 2003, pp. 9-14.
Ghali et al., "The Management of Metatarsus Adductus et Supinatus," The Journal of Bone and Joint Surgery, vol. 66-B, No. 3, May 1984, pp. 376-380.
"Arthrodesis of the Tarsometatarsal Joint," Retrieved from https://musculoskeletalkey.com/arthrodesis-of-the-tarsometatarsal-joint/, posted Apr. 18, 2019, 11 pages.
Dayton, "Tarsal-Metatarsal Joint: Primary & Revision Arthrodesis," Apr. 2014, 38 pages.
Defendant Fusion Orthopedics LLC's Invalidity Contentions, No. CV-22-00490-PHX-SRB, U.S. District Court for the District of Arizona, Aug. 27, 2022, 41 pages.
Prior Art Publications, Exhibit A of Defendant Fusion Orthopedics LLC's Invalidity Contentions, No. CV-22-00490-PHX- SRB, U.S. District Court for the District of Arizona, Aug. 27, 2022, 3 pages.
Claim Chart for Fishco, "Making the Lapidus Easy," The Podiatry Institute (Apr. 2014), Exhibit B1 of Defendant Fusion Orthopedics LLC's Invalidity Contentions, No. CV-22-00490-PHX-SRB, US District Court for the District of Arizona, Aug. 27, 2022, 97 pages.
Claim Chart for Fishco, "A Straightforward Guide to the Lapidus Bunionectomy," HMP Global (Sep. 6, 2013), Exhibit B2 of Defendant Fusion Orthopedics LLC's Invalidity Contentions, No. CV-22-00490-PHX-SRB, US District Court for the District of Arizona, Aug. 27, 2022, 67 pages.
Claim Chart for Groves, "Functional Position Joint Sectioning: Pre-Load Method for Lapidus Arthrodesis," Update 2015: Proceedings of the Annual Meeting of the Podiatry Institute, Chpt. 6, pp. 23-29 (Apr. 2015), Exhibit B3 of Defendant Fusion Orthopedics LLC's Invalidity Contentions, No. CV-22-00490-PHX-SRB, US District Court for the District of Arizona, Aug. 27, 2022, 151 p.
Claim Chart for Mote, "First Metatarsal-Cuneiform Arthrodesis for the Treatment of First Ray Pathology: A Technical Guide," The Journal Foot & Ankle Surgery (Sep. 1, 2009), Exhibit B5 of Defendant Fusion Orthopedics LLC's Invalidity Contentions, No. CV-22-00490-PHX-SRB, US District Court for the District of Arizona, Aug. 27, 2022, 21 pages.
Claim Chart for U.S. Pat. No. 10,376,268 to Fallin et al., entitled "Indexed Tri-Planar Osteotomy Guide and Method," issued Aug. 13, 2019, Exhibit B6 of Defendant Fusion Orthopedics LLC's Invalidity Contentions, No. CV-22-00490- Phx-Srb, US District Court for the District of Arizona, Aug. 27, 2022, 155 pages.
Claim Chart for U.S. Pat. No. 8,282,645 to Lawrence et al., entitled "Metatarsal Bone Implant Cutting Guide," issued Jan. 18, 2010, Exhibit B7 of Defendant Fusion Orthopedics LLC's Invalidity Contentions, No. CV-22-00490-PHX- Srb, US District Court for the District of Arizona, Aug. 27, 2022, 76 pages.
Claim Chart for U.S. Pat. No. 9,452,057 to Dacosta et al., entitled "Bone Implants and Cutting Apparatuses and Methods," issued Apr. 8, 2011, Exhibit B8 of Defendant Fusion Orthopedics LLC's Invalidity Contentions, No. CV-22-00490-PHX-SRB, US District Court for the District of Arizona, Aug. 27, 2022, 110 pages.
Obviousness Chart, Exhibit C of Defendant Fusion Orthopedics LLC's Invalidity Contentions, No. CV-22-00490-PHX- Srb, US District Court for the District of Arizona, Aug. 27, 2022, 153 pages.
"Foot and Ankle Instrument Set," Smith & Nephew, 2013, 2 pages.

(56) References Cited

OTHER PUBLICATIONS

"Lapidus Pearls: Gaining Joint Exposure to Decrease Non-Union," Youtube, Retrieved online from <https://www.youtube.com/watch?v=jqJyE7pj-Y>, dated Nov. 2, 2009, 3 pages.
"Reconstructive Surgery of the Foot & Ankle," The Podiatry Institute, Update 2015, Conference Program, May 2015, 28 pages.
"Speed Continuous Active Compression Implant," BioMedical Enterprises, Inc., A120-029 Rev. 3, 2013, 4 pages.
"Visionaire: Patient Matched Cutting Blocks Surgical Procedure," Smith & Nephew, Inc., 2009, 2 pages.
Arthrex, "Comprehensive Foot System," Retrieved online from <https://www.arthrex.com/resources/animation/8U3iaPvY6kO8bwFAwZF50Q/comprehensive-foot-system?referringTeam=foot_and_ankle>, dated Aug. 27, 2013, 3 pages.
Baravarian, "Why the Lapidus Procedure is Ideal for Bunions," Podiatry Today, Retrieved online from <https://www. hmpglobal-learhmpgloballe.com/site/podipodi/article/5542>, dated May 2006, 8 pages.
Bauer et al., "Offset-V Osteotomy of the First Metatarsal Shaft in Hallux Abducto Valgus," McGlamry's Comprehensive Textbook of Foot and Ankle Surgery, Fourth Edition, vol. 1, Chapter 29, 2013, 26 pages.
Cottom, "Fixation of the Lapidus Arthrodesis with a Plantar Interfragmentary Screw and Medial Low Profile Locking Plate," The Journal of Foot & Ankle Surgery, vol. 51, 2012, pp. 517-522.
Coughlin, "Fixation of the Lapidus Arthrodesis with a Plantar Interfragmentary Screw and Medial Low Profile Locking Plate, "Orthopaedics and Traumatology, vol. 7, 1999, pp. 133-143.
Dayton et al., "Observed Changes in Radiographic Measurements of the First Ray after Frontal Plane Rotation of the First Metatarsal in a Cadaveric Foot Model," The Journal of Foot & Ankle Surgery, vol. 53, 2014, pp. 274-278.
Dayton et al., "Relationship of Frontal Plane Rotation of First Metatarsal to Proximal Articular Set Angle and Hallux Alignment in Patients Undergoing Tarsometatarsal Arthrodesis for Hallux Abducto Valgus: A Case Series and Critical Review of the Literature," The Journal of Foot & Ankle Surgery, 2013, Article in Press, Mar. 1, 2013, 7 pages.
Didomenico et al., "Lapidus Bunionectomy: First Metatarsal-Cuneiform Arthrodesis," McGlamry's Comprehensive Textbook of Foot and Ankle Surgery, Fourth Edition, vol. 1, Chapter 31, 2013, 24 pages.
Fallin et al., US Provisional Application Entitled Indexed Tri-Planar Osteotomy Guide and Method, US Pat. U.S. Appl. No. 62/118,378, filed Feb. 19, 2015, 62 pages.
Fishco, "A Straightforward Guide To The Lapidus Bunionectomy, "Podiatry Today, Retrieved online from <https://www. hmpgloballearningnetwork.com/site/podiatry/blogged/straightforward-guide-lapidus-bunionectomy>, dated Sep. 6, 2013, 5 pages.
Fishco, "Making the Lapidus Easy," The Podiatry Institute, Update 2014, Chapter 14, 2014, pp. 91-93.
Fleming et al., "Results of Modified Lapidus Arthrodesis Procedure Using Medial Eminence as an Interpositional Autograft," The Journal of Foot & Ankle Surgery, vol. 50, 2011, pp. 272-275.
Fuhrmann, "Arthrodesis of the First Tarsometatarsal Joint for Correction of the Advanced Splayfoot Accompanied by a Hallux Valgus," Operative Orthopadie und Traumatologie, No. 2, 2005, pp. 195-210.
Gerard et al., "The Modified Lapidus Procedure," Orthopedics, vol. 31, No. 3, Mar. 2008, 7 pages.

Giannoudis et al., "Hallux Valgus Correction," Practical Procedures in Elective Orthopaedic Surgery, Pelvis and Lower Extremity, Chapter 38, 2012, 22 pages.
Greiner, "The Jargon of Pedal Movements," Foot & Ankle International, vol. 28, No. 1, Jan. 2007, pp. 109-125.
Groves, "Functional Position Joint Sectioning: Pre-Load Method for Lapidus Arthrodesis," The Podiatry Institute, Update 2015, Chapter 6, 2015, pp. 23-29.
Hardy et al., "Observations on Hallux Valgus," The Journal of Bone and Joint Surgery, vol. 33B, No. 3, Aug. 1951, bp. 376-391.
Holmes, Jr., "Correction of the Intermetatarsal Angle Component of Hallux Valgus Using Fiberwire-Attached Endo- buttons," Revista Internacional de Ciencias Podologicas, vol. 6, No. 2, 2012, pp. 73-79.
Integra, "Integra Large Qwix Positioning and Fixation Screw, Surgical Technique," 2012, 16 pages.
Kilmartin et al., "Combined rotation scarf and Akin osteotomies for hallux valgus: a patient focused 9 year follow up of 50 patients," Journal of Foot and Ankle Research, vol. 3, No. 2, 2010, 12 pages.
Lee et al., "Technique Tip: Lateral Soft-Tissue Release for Correction of Hallux Valgus Through a Medial Incision Using A Dorsal Flap Over the First Metatarsal," Foot & Ankle International, vol. 28, No. 8, Aug. 2007, pp. 949-951.
Mote et al., "First Metatarsal-Cuneiform Arthrodesis for the Treatment of First Ray Pathology: A Technical Guide," JFAS Techniques Guide, vol. 48, No. 5, September/Oct. 2009, pp. 593-601.
Myerson, "Cuneiform-Metatarsal Arthrodesis," The Foot and Ankle, Chapter 9, 1997, pp. 107-117.
Sammarco, "Surgical Strategies: Mau Osteotomy for Correction of Moderate and Severe Hallux Valgus Deformity," Foot & Ankle International, vol. 28, No. 7, Jul. 2007, pp. 857-864.
Schon et al., "Cuneiform-Metatarsal Arthrodesis for Hallux Valgus, "The Foot and Ankle, Second Edition, Chapter 8, 2002, pp. 99-117.
Sokoloff, "Lapidus Procedure," Textbook of Bunion Surgery, Chapter 15, 1981, pp. 277-287.
Stamatis et al., "Mini Locking Plate as "Medial Buttress" for Oblique Osteotomy for Hallux Valgus," Foot & Ankle International, vol. 31, No. 10, Oct. 2010, pp. 920-922.
Stewart, "Use for BME Speed Nitinol Staple Fixation for the Lapidus Procedure," date unknown, 1 page.
Wukich et al., "Hypermobility of the First Tarsometatarsal Joint," Foot and Ankle Clinics, vol. 10, No. 1, Mar. 2005, pp. 157-166.
Dayton et al., "Biwinged Excision for Round Pedal Lesions," The Journal of Foot and Ankle Surgery, vol. 35, No. 3, 1996, pp. 244-249.
Dayton et al., "Medial Incision Approach to the First Metatarsophalangeal Joint," The Journal of Foot and Ankle Surgery, vol. 40, No. 6, Nov./Dec. 2001, pp. 414-417.
Dayton et al., "Reduction of the Intermetatarsal Angle after First Metatarsophalangeal Joint Arthrodesis in Patients with Moderate and Severe Metatarsus Primus Adductus," The Journal of Foot and Ankle Surgery, vol. 41, No. 5, Sep./Oct. 2002, pp. 316-319.
Dayton et al., "Use of the Z Osteotomy for Tailor Bunionectomy," The Journal of Foot and Ankle Surgery, vol. 42, No. 3, May/Jun. 2003, pp. 167-169.
Dayton et al., "Early Weightbearing After First Metatarsophalangeal Joint Arthrodesis: A Retrospective Observational Case Analysis," The Journal of Foot and Ankle Surgery, vol. 43, No. 3, May/Jun. 2004, pp. 156-159.
1 Supplementary European Search Report dated Aug. 27, 2023 for corresponding EP Application No. 20862480.

* cited by examiner

PATIENT-SPECIFIC SURGICAL METHODS AND INSTRUMENTATION

CROSS-REFERENCE TO RELATED APPLICATIONS

The present application claims the benefit of U.S. Provisional Patent Application Ser. No. 62/900,294, entitled PATIENT-SPECIFIC SURGICAL METHODS AND INSTRUMENTATION, which was filed on Sep. 13, 2019. The above-referenced application is incorporated by reference herein as though set forth in its entirety.

TECHNICAL FIELD

The present disclosure relates to surgical devices, systems, instruments, and methods. More specifically, the present disclosure relates to patient-specific cutting guides and implants, and methods of designing and using the same.

BACKGROUND

Various bone conditions may be corrected through the use of an osteotomy, in which one or more bones are cut, replaced, and/or reoriented. Cutting guides are often used to help the surgeon properly locate the cut. Unfortunately, many known cutting guides are not patient-specific, and can be difficult to properly position to perform the osteotomy on a specific patient. Even if properly positioned, many known cutting guides are difficult to secure at the desired position, without moving away from the desired position prior to performance of the osteotomy. As a result, many known osteotomy procedures carry risk of an improper cut that fails to correct the underlying condition, or even endangers surrounding tissues.

SUMMARY

The various systems and methods of the present disclosure have been developed in response to the present state of the art, and in particular, in response to the problems and needs in the art that have not yet been fully solved by currently available osteotomy systems and methods.

In some embodiments, a method may be used to correct a condition present in a patient. The method may include obtaining a first bone model of a first bone of one or more bones of the patient's foot, and using at least the first bone model to generate a cutting guide model. The cutting guide model may define a first bone engagement surface shaped to match a first contour on the first bone, and a first guide feature that, with the first bone engagement surface overlying the first contour, is positioned to guide resection of the one or more bones as part of a surgical osteotomy for correcting the condition. The surgical procedure may be selected from a first group consisting of a bunion correction osteotomy, an Evans calcaneal osteotomy, and a medializing calcaneal osteotomy. The first bone may be selected from a second group consisting a metatarsus, a cuneiform, and a calcaneus.

The one or more bones may include the cuneiform and the metatarsus. The surgical osteotomy may be the bunion correction osteotomy. The condition may be a bunion, and the first guide feature may be positioned to guide resection of one of the cuneiform and the metatarsus.

The first bone may be the cuneiform. The first guide feature may be positioned to guide resection of the cuneiform. The cutting guide model may further define a second bone engagement surface shaped to match a second contour of the metatarsus, and a second guide feature that, with the second bone engagement surface overlying the second contour, is positioned to guide resection of the metatarsus.

The method may further include obtaining a second bone model of the metatarsus, and virtually repositioning the second bone model relative to the first bone model to simulate reorientation of the metatarsus relative to the cuneiform to correct the bunion.

The cutting guide model may further include a first end having the first bone engagement surface, a second end having the second bone engagement surface, a first bone attachment feature positioned to secure the first end to the cuneiform, and a second bone attachment feature positioned to secure the second end to the metatarsus.

The method may further include using the cutting guide model to fabricate a cutting guide having the first bone engagement surface, the second bone engagement surface, the first bone attachment feature, the second bone attachment feature, the first guide feature, and the second guide feature.

The method may further include placing the cutting guide such that the first bone engagement surface overlies the first contour and the second bone engagement surface overlies the second contour, securing the first bone attachment feature to the cuneiform, securing the second bone attachment feature to the metatarsus, using the first guide feature to guide motion of a cutter to resect the cuneiform, and using the second guide feature to guide motion of a cutter to resect the metatarsus.

The method may further include reorienting the metatarsus relative to the cuneiform and, after reorienting the metatarsus relative to the cuneiform, promoting fusion between the cuneiform and the metatarsus.

Obtaining the first bone model may include obtaining CT scan data of the first bone. Using the first bone model to generate the cutting guide model may include converting the CT scan data to a CAD models, using the CAD model to obtain the first contour, and using the first contour to generate the first bone engagement surface of the cutting guide model.

The surgical osteotomy may be the Evans calcaneal osteotomy. The first bone may be the calcaneus. The cutting guide model may further have a second bone engagement surface shaped to match a second contour of the calcaneus such that, with the first bone engagement surface overlying the first contour and the second bone engagement surface overlying the second contour, the first guide feature is positioned to guide a cutter to resect the calcaneus to perform the Evans calcaneal osteotomy.

The surgical osteotomy may be the medializing calcaneal osteotomy. The first bone may be the calcaneus. The cutting guide model may further include a second bone engagement surface shaped to match a second contour of the calcaneus such that, with the first bone engagement surface overlying the first contour and the second bone engagement surface overlying the second contour, the first guide feature is positioned to guide a cutter to resect the calcaneus to perform the medializing calcaneal osteotomy.

The method may further include using at least the first bone model to generate an implant model defining a first bone-facing surface with a first shape that matches a first profile of a first resected surface of the first bone after resection of the first bone with a cutting guide fabricated using the cutting guide model.

The implant model may further have a second bone-facing surface with a second shape that matches a second profile of a second resected surface of the first bone or a second bone of the one or more bones after resection of the first bone or a second bone with the cutting guide.

The method may further include using the cutting guide model to fabricate a cutting guide having the first bone engagement surface and first guide feature, using the implant model to fabricate an implant having the first bone-facing surface and the second bone-facing surface, placing the cutting guide such that the first bone engagement surface overlies the first contour, using at least the first guide feature to guide motion of a cutter to resect the one or more bones to define the first resected surface and the second resected surface, and placing the implant between the first resected surface and the second resected surface such that the first shape is aligned with the first profile and the second shape is aligned with the second profile.

According to one embodiment, a system may be provided for correcting a condition present in one or more bones of a patient's foot. The system may have a cutting guide with a first bone engagement surface shaped to match a first contour on a first bone of the one or more bones, and a first guide feature that, with the first bone engagement surface overlying the first contour, is positioned to guide resection of the one or more bones as part of a surgical osteotomy for correcting the condition. The surgical osteotomy may be selected from a first group consisting of a bunion correction osteotomy, an Evans calcaneal osteotomy, and a medializing calcaneal osteotomy. The first bone may be selected from a second group consisting of a metatarsus, a cuneiform, and a calcaneus.

The first bone may be the cuneiform. The surgical osteotomy may be the bunion correction osteotomy. The condition may be a bunion. The first guide feature may be positioned to guide resection of the cuneiform. The cutting guide may further have a second bone engagement surface shaped to match a second contour of the metatarsus, and a second guide feature that, with the second bone engagement surface overlying the second contour, is positioned to guide resection of the metatarsus.

The cutting guide may further have a first end having the first bone engagement surface, a second end having the second bone engagement surface, a first bone attachment feature positioned to secure the first end to the cuneiform, and a second bone attachment feature positioned to secure the second end to the metatarsus.

The surgical osteotomy may be the Evans calcaneal osteotomy or the medializing calcaneal osteotomy. The first bone may be the calcaneus. The cutting guide may further have a second bone engagement surface shaped to match a second contour of the calcaneus such that, with the first bone engagement surface overlying the first contour and the second bone engagement surface overlying the second contour, the first guide feature is positioned to guide a cutter to resect the calcaneus to perform the Evans calcaneal osteotomy or the medializing calcaneal osteotomy.

The system may further have an implant with a first bone-facing surface with a first shape that matches a first profile of a first resected surface of the first bone after resection of the first bone with the cutting guide, and a second bone-facing surface comprising a second shape that matches a second profile of a second resected surface of the first bone or a second bone of the one or more bones after resection of the first bone or a second bone with the cutting guide.

According to some embodiments, a cutting guide may be provided for correcting a bunion present a patient's foot. The cutting guide may have a first bone engagement surface shaped to match a first contour on cuneiform of the patient's foot, and a second bone engagement surface shaped to match a second contour on a metatarsus of the patient's foot. The cutting guide may further have a first slot that, with the first bone engagement surface overlying the first contour and the second bone engagement surface overlying the second contour, is positioned to guide resection of the cuneiform to define a first resected surface on the cuneiform. Further, the cutting guide may have a second slot that, with the first bone engagement surface overlying the first contour and the second bone engagement surface overlying the second contour, is positioned to guide resection of the metatarsus to define a second resected surface on the metatarsus. The first slot and the second slot may be positioned and oriented relative to each other such that, upon fusion of the cuneiform and the metatarsus between the first resected surface and the second resected surface, the bunion is at least partially corrected.

BRIEF DESCRIPTION OF THE DRAWINGS

The advantages, nature, and additional features of exemplary embodiments of the disclosure will become more fully apparent from the following description and appended claims, taken in conjunction with the accompanying drawings. Understanding that these drawings depict only exemplary embodiments and are, therefore, not to be considered limiting of the disclosure's scope, the exemplary embodiments of the disclosure will be described with additional specificity and detail through use of the accompanying drawings in which:

DETAILED DESCRIPTION

Exemplary embodiments of the disclosure will be best understood by reference to the drawings, wherein like parts are designated by like numerals throughout. It will be readily understood that the components, as generally described and illustrated in the Figures herein, could be arranged and designed in a wide variety of different configurations. Thus, the following more detailed description of the embodiments of the apparatus, system, and method, as represented in FIGS. 1A through 11, is not intended to limit the scope of the disclosure but is merely representative exemplary of exemplary embodiments.

The phrases "connected to," "coupled to" and "in communication with" refer to any form of interaction between two or more entities, including mechanical, electrical, magnetic, electromagnetic, fluid, and thermal interaction. Two components may be functionally coupled to each other even though they are not in direct contact with each other. The term "abutting" refers to items that are in direct physical contact with each other, although the items may not necessarily be attached together. The phrase "fluid communication" refers to two features that are connected such that a fluid within one feature is able to pass into the other feature.

The word "exemplary" is used herein to mean "serving as an example, instance, or co illustration." Any embodiment described herein as "exemplary" is not necessarily to be construed as preferred or advantageous over other embodiments. While the various aspects of the embodiments are presented in drawings, the drawings are not necessarily drawn to scale unless specifically indicated.

The present disclosure discloses surgical systems and methods by which a bone condition, such as a deformity, may be corrected through the use of patient-specific instrumentation. Known methods of correcting bone conditions are often limited to a finite range of discretely sized instruments. A patient with an unusual condition, or anatomy that falls between instrument sizes, may not be readily treated with such systems. One example is correction of a bunion, in particular, via adjustment of the angulation between a cuneiform and a metatarsus.

Figures 1A, 1B:
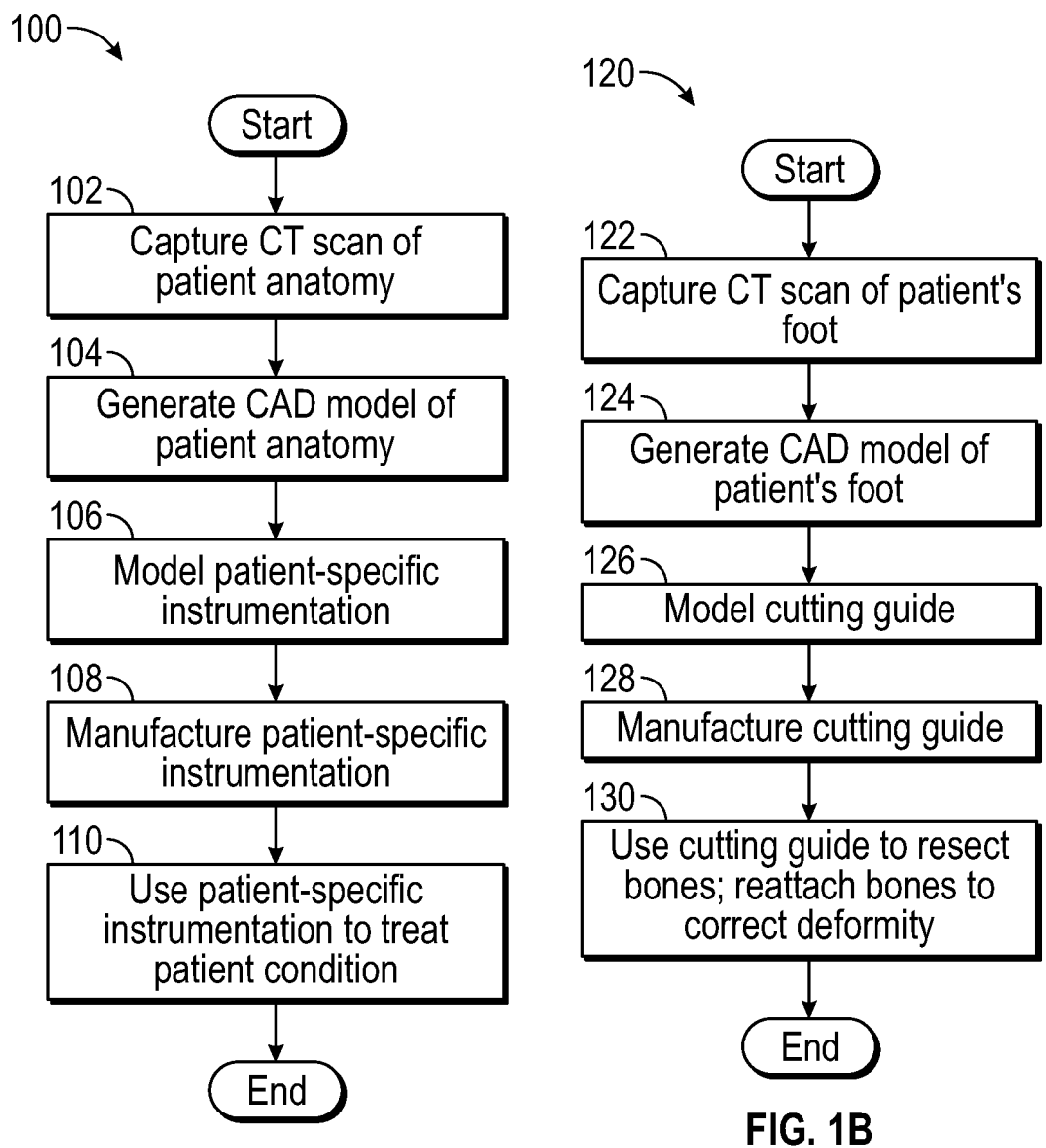
FIG. 1A is a flowchart diagram depicting a method for correcting a bone condition, according to one embodiment.
FIG. 1B is a flowchart diagram depicting a method for correcting bunion deformity u of the human foot, according to one embodiment.

FIG. 1A is a flowchart diagram depicting a method 100 for correcting a bone condition, according to one embodiment. The method 100 may be used for any of a wide variety of bone conditions, including but not limited to deformities, fractures, joint failure, and/or the like. Further, the method 100 may provide correction with a wide variety of treatments, including but not limited to arthroplasty, arthrodesis, fracture repair, and/or the like.

As shown, the method 100 may begin with a step 102 in which a CT scan (or another three-dimensional image) of the patient's anatomy is obtained. The step 102 may entail capturing a scan of only the particular bone(s) to be treated, or may entail capture of additional anatomic information, such as the surrounding tissues. Additionally or alternatively, the step 102 may entail receiving a previously captured image, for example, at a design and/or fabrication facility. Performance of the step 102 may result in possession of a three-dimensional model of the patient's anatomy, or three-dimensional surface points that can be used to construct such a three-dimensional model.

After the step 102 has been carried out, the method 100 may proceed to a step 104 in which a CAD model of the patient's anatomy is generated. The CAD model may be of any known format, including but not limited to SolidWorks, Catia, AutoCAD, or DXF. In some embodiments, customized software may be used to generate the CAD model from the CT scan. The CAD model may only include the bone(s) to be treated or may include surrounding tissues. In alternative embodiments, the step 104 may be omitted, as the CT scan may capture data that can directly be used in future steps without the need for conversion.

In a step 106, the CAD model and/or CT scan data may be used to model patient-specific instrumentation that can be used to correct the condition, as it exists in the patient's anatomy. In some embodiments, any known CAD program may be used to view and/or manipulate the CAD model and/or CT scan, and generate one or more instruments that are matched specifically to the size and/or shape of the patient's bone(s). In some embodiments, such instrumentation may include a cutting guide that is attachable to one or more bones, with one or more guide features that facilitate resection of the one or more bones pursuant to a procedure such as arthroplasty or arthrodesis. In some embodiments, performance of the step 106 may include modelling an instrument with a bone apposition surface that is shaped to match the contour of a surface of the bone, such that the bone apposition surface can lie directly on the corresponding contour.

In a step 108, the model(s) may be used to manufacture patient-specific instrumentation and/or implants. This may be done via any known manufacturing method, including casting, forging, milling, additive manufacturing, and/or the like. Additive manufacturing may provide unique benefits, as the model may be directly used to manufacture the necessary instrumentation and/or implants (without the need to generate molds, tool paths, and/or the like beforehand). Such instrumentation may optionally include a cutting guide with the bone apposition surface and one or more guide features as described above.

In addition to or in the alternative to the step 108, the model(s) may be used to select from available sizes of implants and/or instruments and advise the surgeon accordingly. For example, where a range of cutting guides are available for a given procedure, analysis of the CAD data may facilitate pre-operative selection of the optimal cutting guide and/or optimal placement of the cutting guide on the bone. Similarly, if a range of implants may be used for a given procedure, analysis of the CAD data may facilitate pre-operative selection of the optimal implant(s). More particularly, properly-sized spacers, screws, bone plates, and/or other hardware may be pre-operatively selected.

Thus, the result of the step 108 may be provision, to the surgeon, of one or more of the following: (1) one or more patient-specific instruments; (2) one or more patient-specific implants; (3) an instrument, selected from one or more available instrument sizes and/or configurations; (4) an implant, selected from one or more available implant sizes and/or configurations; (5) instructions for which instrument(s) to select from available instrument sizes and/or configurations; (6) instructions for which implant(s) to select from available implant sizes and/or configurations; (7) instructions for proper positioning or anchorage of one or more instruments to be used in the procedure; and (8) instructions for proper positioning or anchorage of one or more implants to be used in the procedure. These items may be provided to the surgeon directly, or to a medical device company or representative, for subsequent delivery to the surgeon.

In a step 110, the manufactured instrumentation may be used in surgery to facilitate treatment of the condition. In some embodiments, this may entail placing the modelled bone apposition surface against the corresponding contour of the bone used to obtain its shape, and then using the guide feature(s) to guide resection of one or more bones. Then the bone(s) may be further treated, for example, by attaching one or more joint replacement implants (in the case of joint arthroplasty), or by attaching bone segments together (in the case of arthrodesis or fracture repair). Prior to completion of the step 110, the instrumentation may be removed from the patient, and the surgical wound may be closed.

As mentioned previously, the method 100 may be used to correct a wide variety of bone conditions. One particular example of the method 100 will be shown and described in connection with FIG. 1B, for correction of a bunion deformity of the foot.

FIG. 1B is a flowchart diagram depicting a method 120 for correcting bunion deformity of the human foot, according to one embodiment. The method 120 may be used to carry out an arthrodesis procedure by which the first metatarsocuneiform joint is removed and the first cuneiform and first metatarsus are secured together in a manner that properly aligns the first metatarsus, providing correction of the deformity.

As shown, the method 120 may begin with a step 122 in which a CT scan (or another three-dimensional image) of the patient's foot is obtained. The step 122 may entail capturing a scan of only the first cuneiform and first metatarsus, or may entail capture of additional anatomic information, such as the entire foot. Additionally or alternatively, the step 122 may entail receipt of previously captured image data. Capture of the entire foot in the step 122 may facilitate proper alignment of the first metatarsus with the rest of the foot (for example, with the second metatarsus). Performance of the step 122 may result in generation of a three-dimensional model of the patient's foot, or three-dimensional surface points that can be used to construct such a three-dimensional model.

After the step 122 has been carried out, the method 120 may proceed to a step 124 in which a CAD model of the relevant portion of the patient's anatomy is generated. The CAD model may optionally include the bones of the entire foot, like the CT scan obtained in the step 122. In alternative embodiments, the step 124 may be omitted in favor of direct utilization of the CT scan data, as described in connection with the step 104.

In a step 126, the CAD model and/or CT scan data may be used to model patient-specific instrumentation that can be used to correct the bunion deformity. Such instrumentation may include a cutting guide that is attachable to the first cuneiform and the first metatarsus, with two guide features that facilitate resection of the cuneiform and the metatarsus in preparation for arthrodesis. In some embodiments, performance of the step 126 may include modelling the cutting guide with a bone apposition surface that is shaped to match contours of the surfaces of the cuneiform and the metatarsus, such that the bone apposition surface can lie directly on the corresponding contours of the first cuneiform and the first metatarsus.

In a step 128, the model(s) may be used to manufacture patient-specific instrumentation and/or instruments. This may include manufacturing the cutting guide with the bone apposition surface and the guide features as described above. As in the step 108, the step 128 may additionally or alternatively involve provision of one or more instruments and/or implants from among a plurality of predetermined configurations or sizes. Further, the step 128 may additionally or alternatively involve provision of instructions for placement and/or anchorage of one or more instruments and/or instruments to carry out the procedure.

In a step 130, the manufactured cutting guide may be used in surgery to facilitate treatment of the condition. Specifically, the bone apposition surface of the cutting guide may be placed against the corresponding contours of the first cuneiform and the first metatarsus. The guide features (for example, slots) may then be positioned on either side of the joint between the first cuneiform and the first metatarsus to guide resection of the first metatarsus and the first cuneiform to remove the intervening joint. The cutting guide may then be removed, and the remaining portions of the first cuneiform and the first metatarsus may be placed to abut each other. The cutting guide may have been shaped such that the cuts made to the first cuneiform and the first metatarsus are properly oriented to bring the first metatarsus back into its proper orientation relative to the rest of the foot. The first cuneiform and the first metatarsus may be secured together through the use of a bone plate or the like. The surgical wound may be closed to allow the foot to heal, and to allow the first cuneiform and the first metatarsus to fuse together.

The method 100 and the method 120 are merely exemplary. Those of skill in the art will recognize that various steps of the method 100 and the method 120 may be reordered, omitted, and/or supplemented with additional steps not specifically shown or described herein.

As mentioned previously, the method 120 is only one species of the method 100; the present disclosure encompasses many different procedures, performed with respect to many different bones and/or joints of the body. Exemplary steps and instrumentation for the method 120 will further be shown and described in connection with FIGS. 2 through 7D. Those of skill in the art will recognize that the method 120 may be used in connection with different instruments; likewise, the instruments of FIGS. 2 through 7D may be used in connection with methods different from the method 100 and the method 120.

Figure 2:
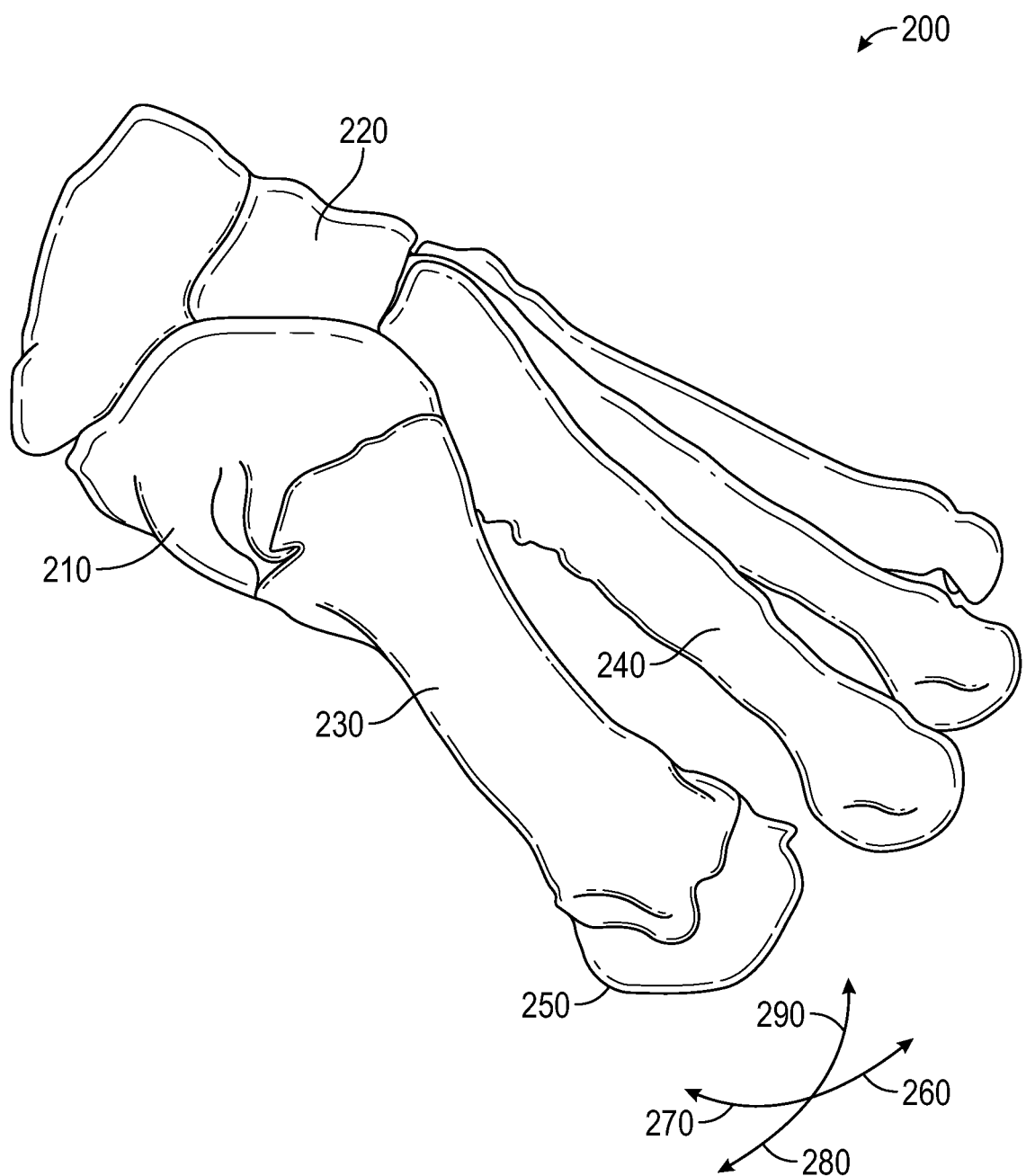
FIG. 2 is a perspective view of a portion of a foot with a bunion deformity to be treated through use of the methods of FIGS. 1A and/or 1B, according to one embodiment.
Figure 3A:
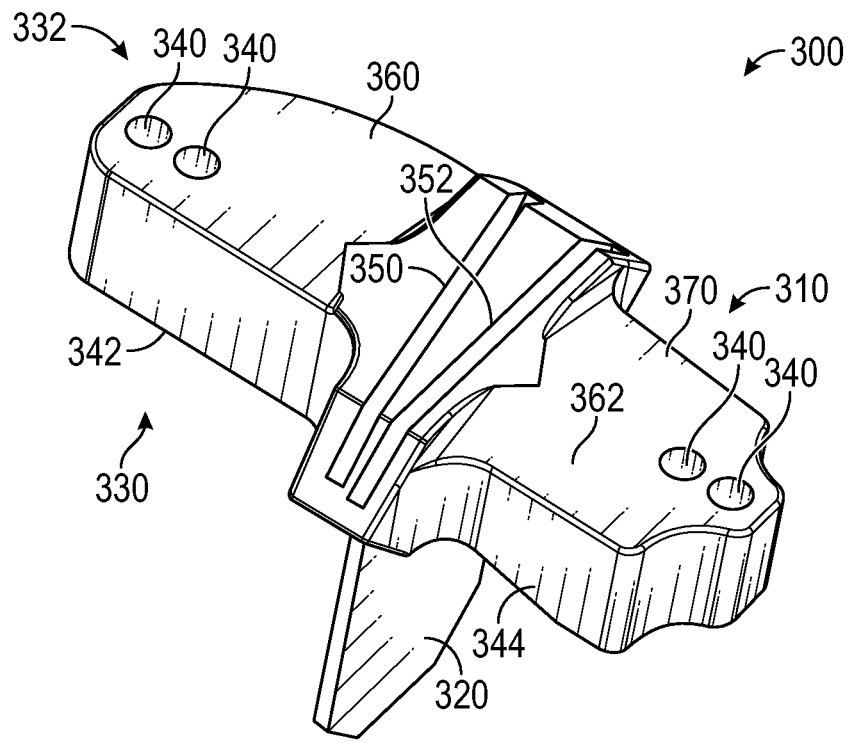
FIGS. 3A, 3B, 3C, and 3D are top perspective, alternative top perspective, front elevation, and bottom perspective views, respectively, of a patient-specific cutting guide, according to one embodiment
Figure 3B:
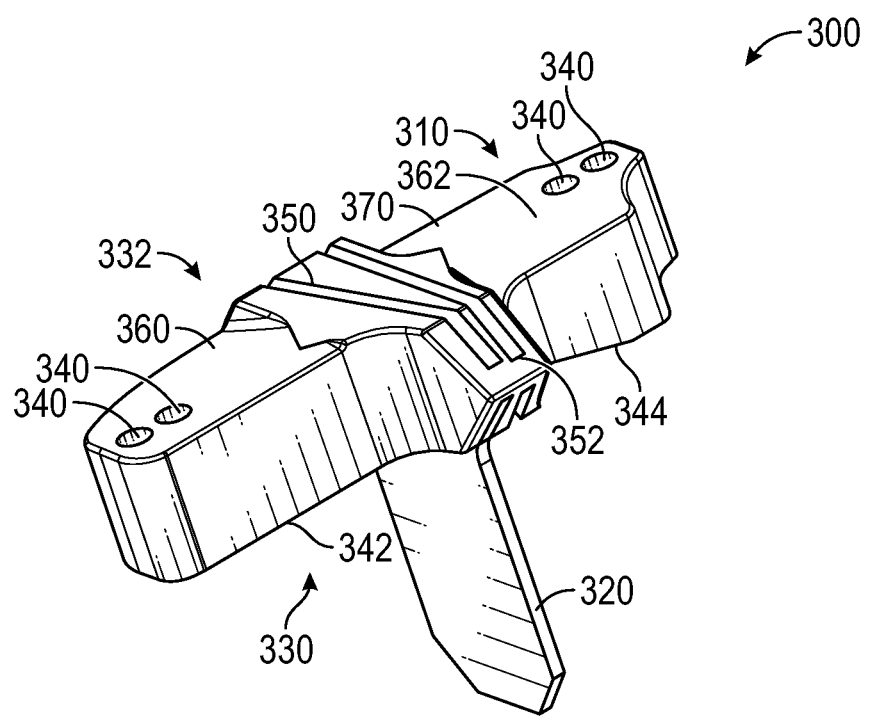
Figure 3C:
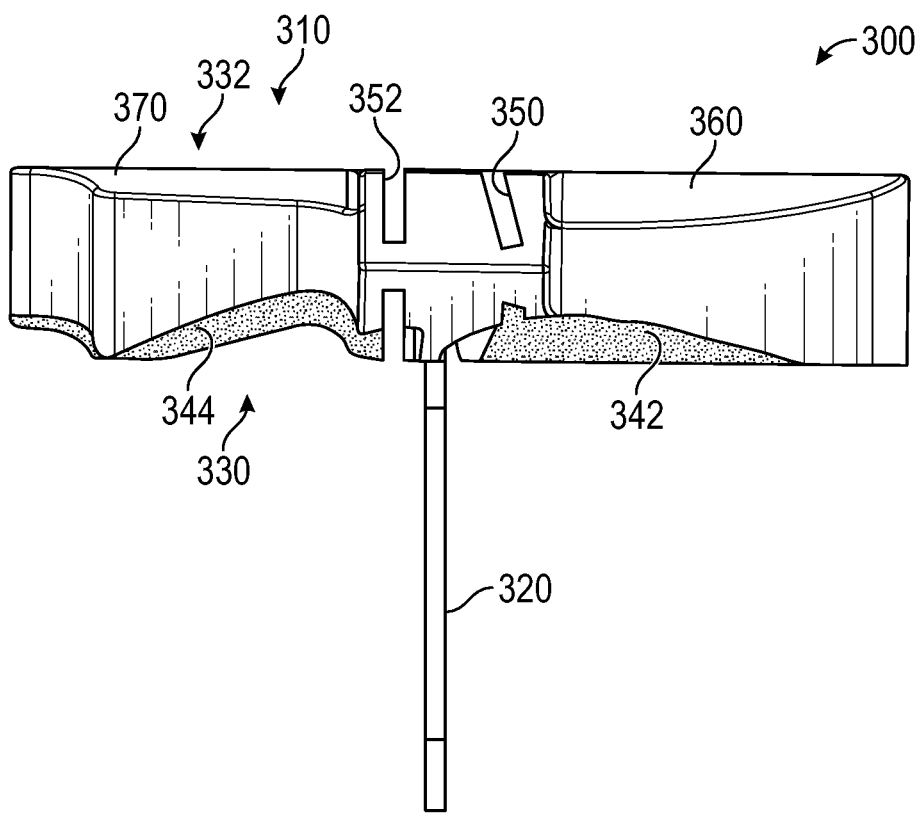
Figure 3D:
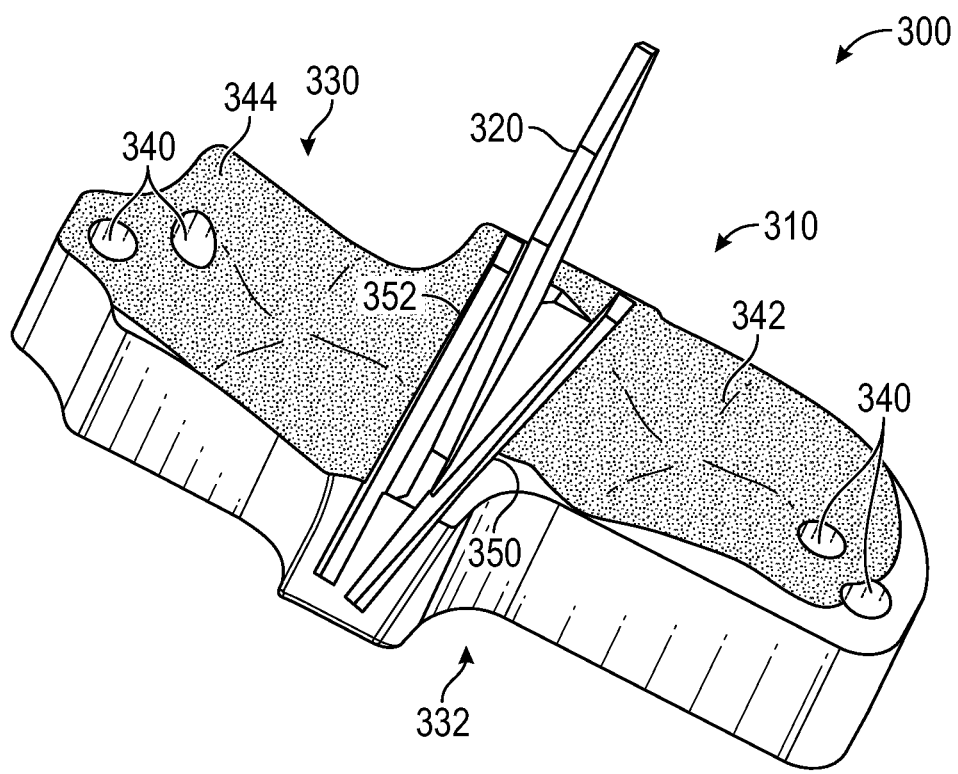

FIG. 2 is a perspective view of a portion of a foot 200 with a bunion deformity to be treated through use of the method 100 (and more specifically, the method 120) described above. The foot 200 may have a first cuneiform 210, a second cuneiform 220, a first metatarsus 230, and a second metatarsus 240. The first cuneiform 210 and the second cuneiform 220 may be joined together at a first metatarsocuneiform joint, and the first metatarsus 230 and the second metatarsus 240 may be joined together at a second metatarsocuneiform joint.

The first metatarsus 230 may be excessively angled in a medial direction 270 (i.e., toward the lower left-hand corner of the page), causing a painful protrusion at a distal end 250 of the first metatarsus 230, and further causing the phalanges (not shown) attached to the distal end 250 to be angled excessively in a lateral direction 260 (i.e., pointing toward the other phalanges of the foot, rather than pointing directly forward). The excessive medial angulation of the first metatarsus 230 may also result in an excessive gap between the first metatarsus 230 and the second metatarsus 240.

The first metatarsus 230 may further be offset in a plantar direction 280 or in a dorsal direction 290, relative to the remainder of the foot 200. Accordingly, the orientation of the first metatarsus 230 may need to be adjusted to move the distal end 250 in the lateral direction 260 and in the plantar direction 280 and/or in the dorsal direction 290.

Every deformity is different; accordingly, the degree of angular adjustment needed in each direction may be different for every patient. Use of a patient-specific cutting guide may help the surgeon obtain the optimal realignment in the lateral direction 260 and in the plantar direction 280 or the dorsal direction 290. Conversely, use of one of a number of differently-sized cutting guides may provide only approximate correction, as the surgeon may not have a guide that precisely matches the correction needed for the foot 200, and must thus choose the cutting guide that most closely provides the desired correction. Such differently sized cutting guides would not be contoured to fit the first cuneiform 210 or the first metatarsus 230, thus introducing additional potential for error as the surgeon must properly align the selected cutting guide.

Thus, providing a patient-specific cutting guide may provide unique benefits. Specifically, the patient-specific cutting guide may provide precise correction of the deformity present in the foot 200 and may also reduce the likelihood of improper correction due to misalignment of the cutting guide on the foot 200. The optimal cut provided by such a cutting guide may further reduce the likelihood that additional procedures, such as attachment of the first metatarsus 230 to the second metatarsus 240 to each other with screws or the like, will be needed to provide the desired correction. Any such additional procedure carries its own added surgical burden and risk of failure. Thus, the use of patient-specific instrumentation may shorten surgery, accelerate recovery, and reduce the risk of complications.

FIGS. 3A, 3B, 3C, and 3D are top perspective, alternative top perspective, front elevation, and bottom perspective views, respectively, of a patient-specific cutting guide, or cutting guide 300, according to one embodiment. The cutting guide 300 may be designed to facilitate resection of the first cuneiform 210 and the first metatarsus 230 with planar cuts at the proper angles to provide dual-plane correction of the orientation of the first metatarsus 230, thereby providing correction in the lateral direction 260 and in the plantar direction 280 or the dorsal direction 290.

As shown, the cutting guide 300 may have a body 310 with a monolithic construction and the general shape of a rectangular prism. The cutting guide 300 may further have a joint alignment feature that helps align the body 310 with the metatarsocuneiform joint between the first cuneiform 210 and the first metatarsus 230. The joint alignment feature may consist of a joint probe 320 that extends from the body 310 and has a blade-like shape. The body 310 may reside on the dorsal surfaces of the first cuneiform 210 and the first metatarsus 230, while the joint probe 320 may protrude into the metatarsocuneiform joint between the first cuneiform 210 and the first metatarsus 230 to provide proper alignment of the body 310 with the metatarsocuneiform joint.

The body 310 may have a bone apposition side 330 that, upon attachment of the body 310 to the first cuneiform 210 and the first metatarsus 230, is to face toward the first cuneiform 210 and the first metatarsus 230. The body 310 may also have an outward-facing side 332 that, upon attachment of the body 310 to the first cuneiform 210 and the first metatarsus 230, faces outward, away from the first cuneiform 210 and the first metatarsus 230. Further, the body 310 may have one or more bone attachment features that facilitate attachment of the body 310 to the first cuneiform 210 and/or the first metatarsus 230. Such bone attachment features may comprise any of a wide variety of holes, spikes, fastening devices, and/or the like. As embodied in FIGS. 3A through 3D, the bone attachment features may take the form of holes 340 that extend from the bone apposition side 330 to the outward-facing side 332. The holes 340 may be shaped to accommodate pins, K-wires, and/or other elongated bone fixation elements that can be anchored in the first cuneiform 210 and/or the first metatarsus 230 to keep the cutting guide 300 in place.

The bone apposition side 330 may be custom contoured to match the shapes of the first cuneiform 210 and/or the first metatarsus 230. As embodied in FIGS. 3A through 3D, the bone apposition side 330 may have a cuneiform apposition portion 342 shaped to lie against the dorsal surface of the first cuneiform 210, and a metatarsus apposition portion 344 shaped to lie against the dorsal surface of the first metatarsus 230. As shown, the cuneiform apposition portion 342 may be contoured to match the contour of the dorsal surface of the first cuneiform 210 on which it is to rest, and the metatarsus apposition portion 344 may similarly be contoured to match the contour of the dorsal surface of the first metatarsus 230 on which it is to rest. Thus, the body 310 may have only one stable position and orientation relative to the first cuneiform 210 and the first metatarsus 230.

Generation of the contours of the cuneiform apposition portion 342 and the metatarsus apposition portion 344 may be performed relative easily in various CAD programs. In some embodiments, the shapes of the corresponding dorsal surfaces of the first cuneiform 210 and the first metatarsus 230 may be obtained directly from the CAD models and/or CT scan data, and simply copied onto the model for the body 310 of the cutting guide 300. Various operations may be used to copy surfaces from one object to another. Additionally or alternatively, various Boolean operations, such as a Boolean subtraction operation, may be used to remove material from a model for the body 310 with a shape that matches the dorsal surfaces of the first cuneiform 210 and the first metatarsus 230.

The body 310 may further have guide features that guide a cutter to resect the first cuneiform 210 and the first metatarsus 230 in the manner needed to make the desired correction. For example, the guide features may be used to guide a planar cutting blade, an arcuate cutting blade, a drill or mill, a burr, and/or the like.

In the embodiment of FIGS. 3A through 3D, the guide features may guide a reciprocating planar blade, such as that of a surgical bone saw, that forms planar cuts in the first cuneiform 210 and the first metatarsus 230. Thus, the guide features may take the form of a first slot 350 and a second slot 352, which may be positioned toward the center of the body 310, on opposite sides of the joint probe 320. Thus, upon proper positioning of the cutting guide 300, the first slot 350 may be positioned over the first cuneiform 210 to facilitate resection of the first cuneiform 210, while the second slot 352 may be positioned over the first metatarsus 230 to facilitate resection of the first metatarsus 230.

In alternative embodiments, a guide feature may be designed to guide a different type cutter, such as a drill, mill, or side-cutting burr. In such embodiments, the guide feature may not be a slot, but may instead be a translatable or rotatable cutter retainer that guides translation and/or rotation of the cutter relative to the bone.

Returning to FIGS. 3A through 3D, the body 310 may further have features that facilitate proper positioning of the cutting guide 300 on the first cuneiform 210 and the first metatarsus 230. More specifically, the body 310 may have a first bone indicator 360 with the text "CUN," indicating that the end of the body 310 with the first bone indicator 360 is to be positioned over the first cuneiform 210. Similarly, the body 310 may have a second bone indicator 362 with the text "MET," indicating that the end of the body 310 with the second bone indicator 362 is to be positioned over the first metatarsus 230. In addition, the body 310 may have a side indicator 370 with the text "LEFT," indicating that the cutting guide 300 is to be used in connection with the patient's left foot. The side indicator 370 may be particularly helpful when bunion corrections are to be provided on both of the patient's feet. In such a case, the surgeon may manufacture or receive two separate cutting guides: one for the left foot (the foot 200 of FIG. 2) and another for the right foot (not shown).

Figure 4:
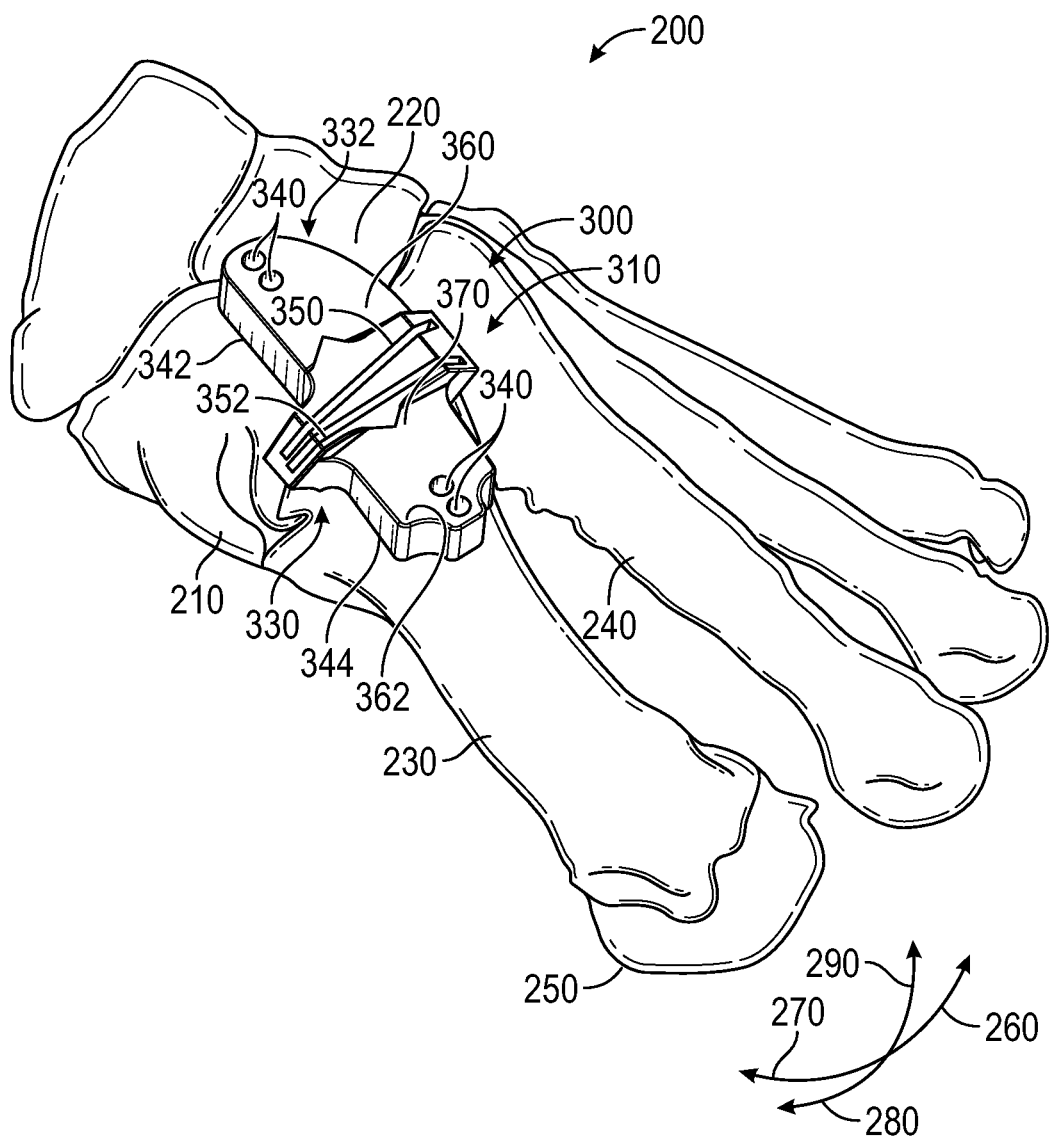
FIG. 4 is a perspective view of the foot of FIG. 2, with the cutting guide of FIGS. 3A, 3B, 3C and 3D properly positioned on the first cuneiform and the first metatarsus, but as yet not attached to the first cuneiform and the first metatarsus.

FIG. 4 is a perspective view of the foot 200 of FIG. 2, with the cutting guide 300 of FIGS. 3A, 3B, 3C and 3D properly positioned on the first cuneiform 210 and the first metatarsus 230, but as yet not attached to the first cuneiform 210 and the first metatarsus 230. The surgeon has made the necessary incision(s) to expose the dorsal surfaces of the first cuneiform 210 and the first metatarsus 230, and has inserted the cutting guide 300 such that the cuneiform apposition portion 342 (identified by the first bone indicator 360 on the outward-facing side 332 of the body 310) is resting on the corresponding dorsal surface of the first cuneiform 210, and the metatarsus apposition portion 344 (identified by the second bone indicator 362 on the outward-facing side 332 of the body 310) is resting on the corresponding dorsal surface of the first metatarsus 230. Since the cuneiform apposition portion 342 and the metatarsus apposition portion 344 are contoured to match the bone surfaces on which they rest, the body 310 may readily slide into its proper position on the first cuneiform 210 and the first metatarsus 230.

Notably, the joint probe 320 (not visible) may reside between the first cuneiform 210 and the first metatarsus 230 (i.e., distal to the first cuneiform 210 and proximal to the first metatarsus 230). The surgeon may need to cut the metatarsocuneiform joint between the first cuneiform 210 and the first metatarsus 230 to form a space between the first cuneiform 210 and the first metatarsus 230 to receive the joint probe 320. Positioning the joint probe 320 in this space may further help to ensure that the cutting guide 300 is properly aligned relative to the first cuneiform 210 and the first metatarsus 230.

Figure 5:
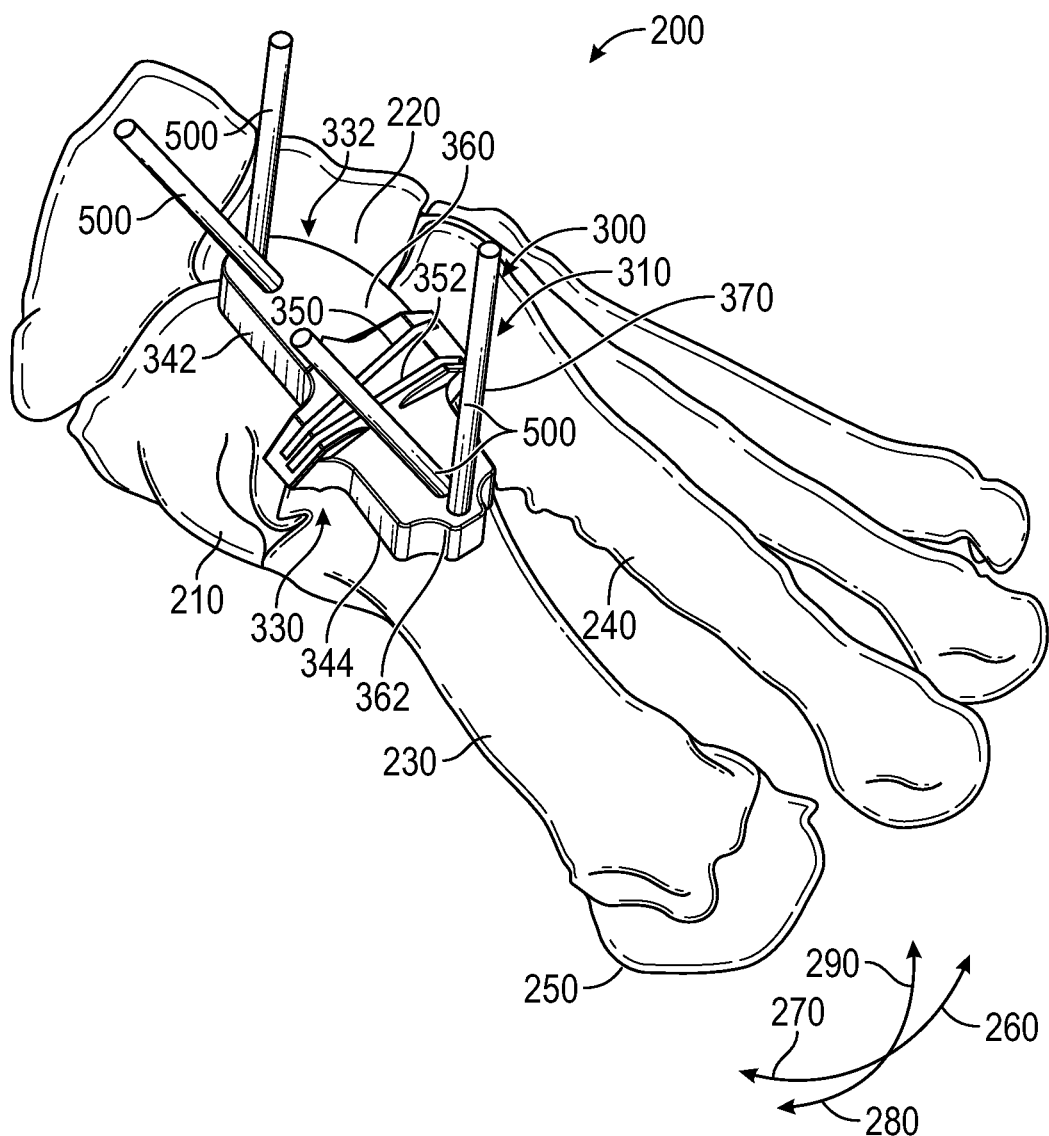
FIG. 5 is a perspective view of the foot of FIG. 2, with the cutting guide of FIGS. 3A, 3B, 3C, and 3D properly positioned on the first cuneiform and the first metatarsus, and attached to the first cuneiform and the first metatarsus in preparation for resection of the first cuneiform and the first metatarsus, according to one embodiment.

FIG. 5 is a perspective view of the foot 200 of FIG. 2, with the cutting guide 300 of FIGS. 3A, 3B, 3C, and 3D properly positioned on the first cuneiform 210 and the first metatarsus 230, and attached to the first cuneiform 210 and the first metatarsus 230 in preparation for resection of the first cuneiform 210 and the first metatarsus 230. Specifically, pins 500 may be inserted through the holes 340 in the body 310 and anchored in the first cuneiform 210 and the first metatarsus 230. Each of the pins 500 may have a sharp and/or threaded distal end that can penetrate and/or readily be retained in the bone of the first cuneiform 210 or the first metatarsus 230. Additionally or alternatively, a drill or other hole-forming instrument may be used to pre-form holes in the first cuneiform 210 and/or the first metatarsus 230 to receive the distal ends of the pins 500.

As shown, the body 310 may have two holes 340 positioned over the first cuneiform 210, and two holes 340 positioned over the first metatarsus 230. This is merely exemplary; in some embodiments, a cutting guide may be secured to only one of the first cuneiform 210 and the first metatarsus 230, or may be secured to either of the first cuneiform 210 and the first metatarsus 230 with only one pin 500, or with more than two pins 500. Further, in some alternative embodiments, different fasteners may be used, such as screws, clamps, clips, and/or the like.

Once the cutting guide 300 has been secured relative to the first cuneiform 210 and the first metatarsus 230, the first cuneiform 210 and the first metatarsus 230 may be resected. In some embodiments, a reciprocating blade may be inserted into the first slot 350 and moved medially and laterally, between opposite ends of the first slot 350, to make a planar cut that removes the distal end of the first cuneiform 210. Similarly, the reciprocating blade (or a different reciprocating blade) may be inserted into the second slot 352 and moved medially and laterally, between opposite ends of the second slot 352, to make a planar cut that removes the proximal end of the first metatarsus 230. The cuts in the first cuneiform 210 and the first metatarsus 230 may be made in either order. In either case, once both cuts are made, the metatarsocuneiform joint between the first cuneiform 210 and the first metatarsus 230 may be removed, resulting in exposure of "bleeding" bone at the distal end of the first cuneiform 210 and the proximal end of the first metatarsus 230. The cutting guide 300 may be removed, along with some or all of the pins 500. If desired, at least two of the pins 500 may remain in place and used to attach a distractor (not shown) to the first cuneiform 210 and the first metatarsus 230, such that the distractor can temporarily widen the space between the first cuneiform 210 and the first metatarsus 230 to allow for fenestration and/or other preparation of the cut surfaces of the first cuneiform 210 and the first metatarsus 230. Once such preparation has been carried out, the remaining pins 500 may also be removed.

The resulting bleeding and/or prepared bone may readily grow together and fuse, upon abutment of the distal end of the first cuneiform 210 to the proximal end of the first metatarsus 230, particularly with application of some compression across the juncture of the two bones. Since the positions and orientations of the first slot 350 and the second slot 352 were carefully selected to provide the proper correction, the first metatarsus 230 may be positioned to abut the first cuneiform 210, resulting in reorientation of the first metatarsus 230 to a desired orientation, relative to the lateral direction 260 and the plantar direction 280 and/or the dorsal direction 290. Further, the surgeon may optionally rotate the first metatarsus 230, relative to the first cuneiform 210, about an axis perpendicular to the cutting planes, if desired.

Figure 6A:
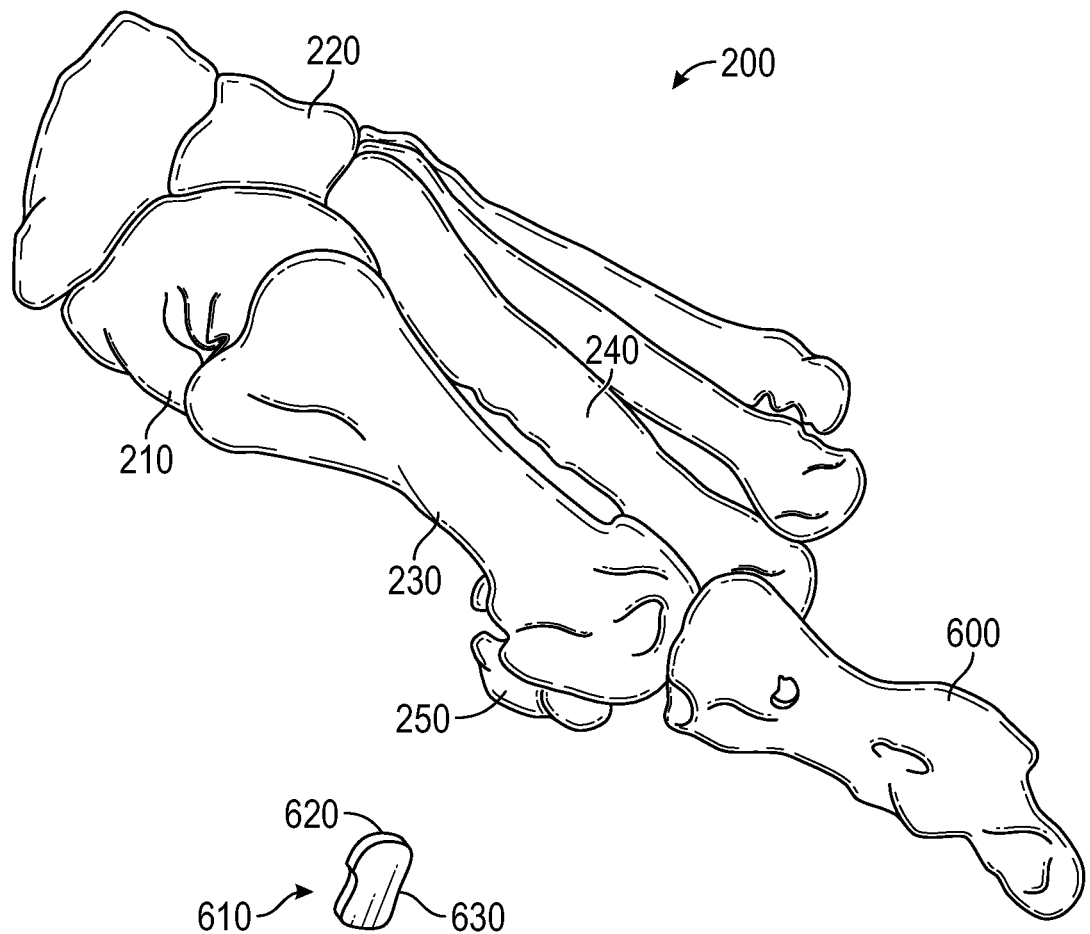
FIG. 6A is a perspective view of the foot of FIG. 2, after resection of the first cuneiform and the first metatarsus, removal of the cutting guide, and placement of the first metatarsus to abut the first cuneiform, according to one embodiment.

FIG. 6A is a perspective view of the foot 200 of FIG. 2, after resection of the first cuneiform 210 and the first metatarsus 230, removal of the cutting guide 300, and placement of the first metatarsus 230 to abut the first cuneiform 210. As shown, the distal end 250 of the first metatarsus 230 may now be positioned much closer to the second metatarsus 240, in a more natural position. Further, FIG. 6A depicts a first proximal phalanx 600, which may now be properly oriented generally parallel to the other phalanges (not shown), rather than pointing in the lateral direction 260. If desired, further steps may be performed relative to the joint between the first metatarsus 230 and the first proximal phalanx 600 in order to keep them in the proper relative orientation. The distal end 250 may also have been shifted in the plantar direction 280 or in the dorsal direction 290 from the position of FIG. 2. Thus, the desired dual-plane correction of the orientation of the first metatarsus 230 may be complete.

The first metatarsus 230 may be secured to the first cuneiform 210, at least until proper bone in-growth has occurred between the first cuneiform 210 and the first metatarsus 230. In some embodiments, a bone plate (not shown) or other fastener (not shown) may be used to secure the first cuneiform 210 and the first metatarsus 230 together. Additional hardware (not shown) may be used to stabilize the position and/or orientation of the first proximal phalanx 600 relative to the first metatarsus 230, if desired. The surgical wound may be closed, and the foot 200 may be allowed to heal with the bunion deformity corrected.

Figure 6B:
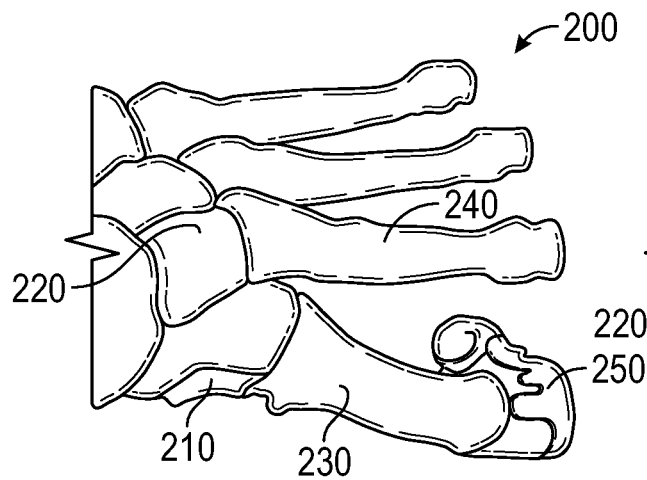
FIGS. 6B and 6C are dorsal views of the foot of FIG. 2, before and after correction, respectively, according to one embodiment.
Figure 6C:
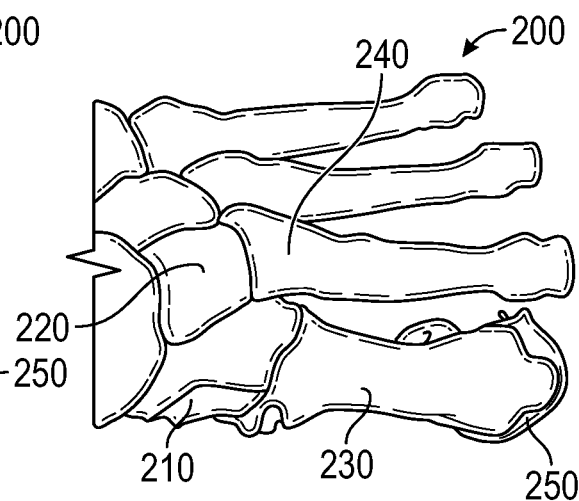
Figure 7A:
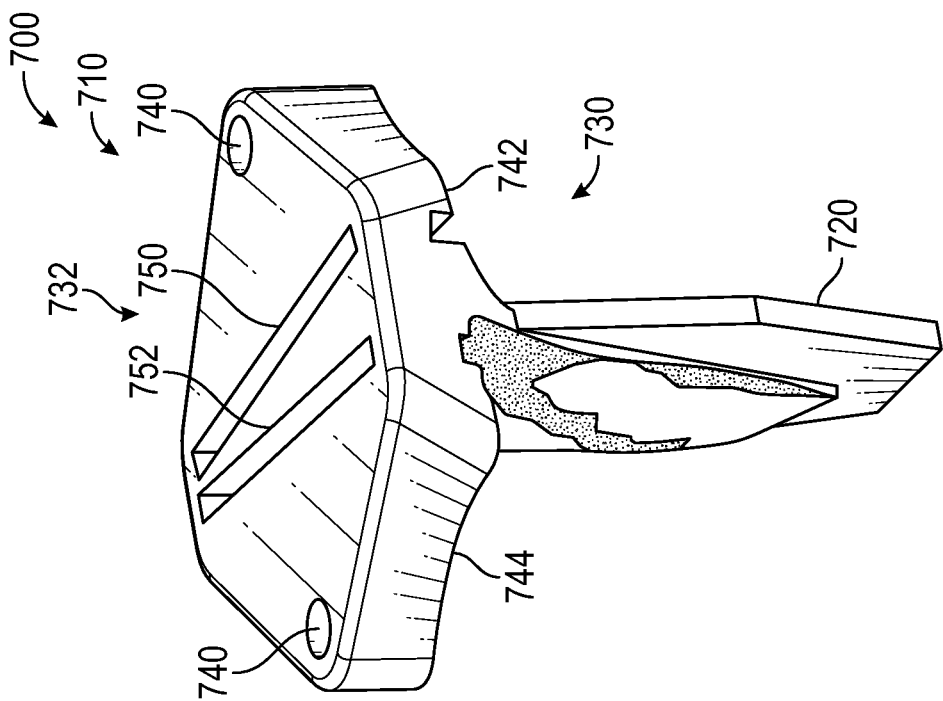
FIGS. 7A, 7B, 7C, and 7D are top perspective, alternative top perspective, front elevation, and bottom perspective views, respectively, of a patient-specific cutting guide according to one alternative embodiment.
Figure 7B:
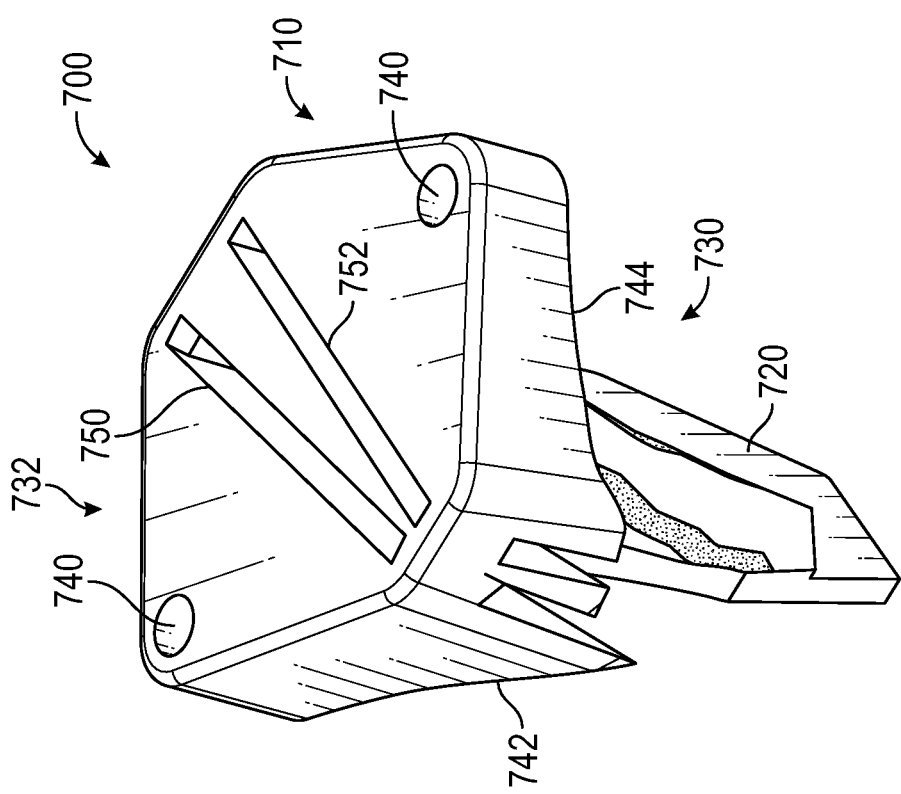
Figure 7C:
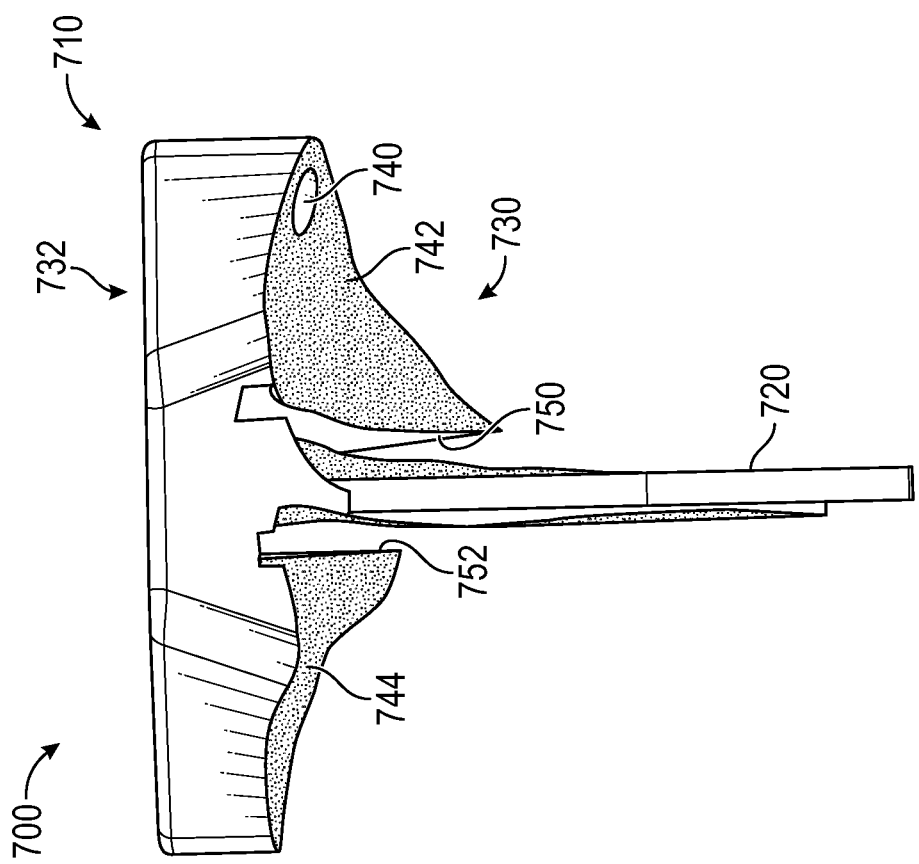
Figure 7D:
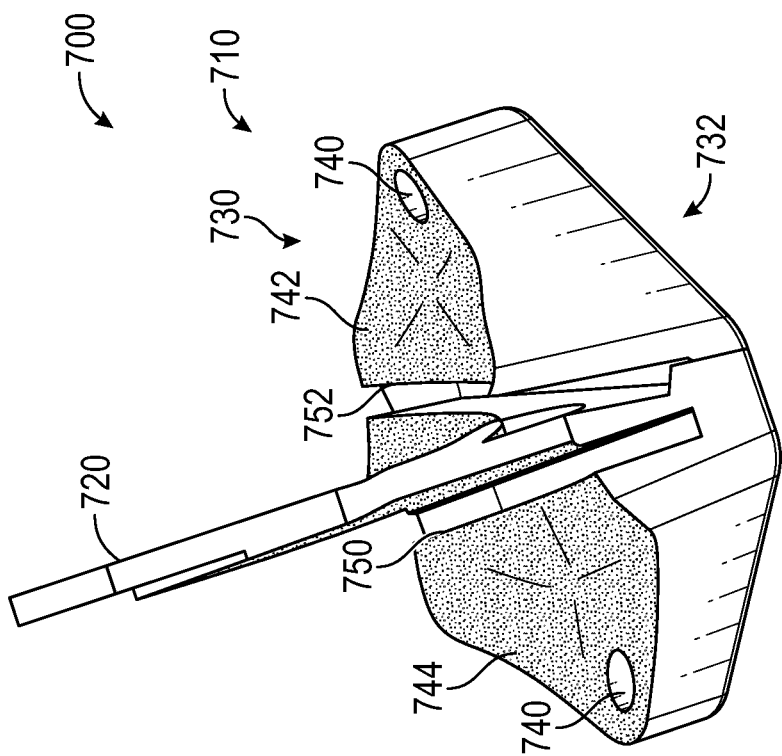

FIGS. 6B and 6C are dorsal views of the foot 200, before and after correction, respectively. FIGS. 6B and 6C illustrate the correction of the angulation of the first metatarsus 230, by which the distal end 250 of the first metatarsus 230 is moved in the lateral direction 260. In some embodiments, an implant 610 may be inserted in the space between the first metatarsus 230 and the first cuneiform 210 in order hold the first metatarsus 230 and the first cuneiform 210 together and/or facilitate bony fusion between the first metatarsus 230 and the first cuneiform 210.

In some embodiments, the implant 610 may be patient-specific. For example, the implant 610 may have a cuneiform-facing side 620 that is shaped and/or sized to be secured to the adjoining, resected surface of the first cuneiform 210, and a metatarsus-facing side 630 that is shaped and/or sized to be secured to the adjoining, resected surface of the first metatarsus 230. As the resections made to the first metatarsus 230 and the first cuneiform 210 may both planar, the cuneiform-facing side 620 and/or the metatarsus-facing side 630 may also be planar. However, the cuneiform-facing side 620 and/or the metatarsus-facing side 630 may advantageously each be shaped to match the profile of the resected surface of the first cuneiform 210 and the first metatarsus 230, respectively.

This shaping may be accomplished by custom-designing the implant 610 for the patient, using the same models (for example, from CT scans) of the first metatarsus 230 and the first cuneiform 210 that were used to generate the cutting guide 300. Thus, the implant 610 may have a shape that provides secure attachment and/or fusion between the first metatarsus 230 and the first cuneiform 210 while avoiding proud edges or other protruding features that could otherwise interfere with surrounding tissues.

As indicated previously, the cutting guide 300 is only one of many patient-specific instruments that may be used in connection with the method 100 and/or the method 120. An alternative cutting guide suitable for use with the method 120 will be shown and described in connection with FIGS. 7A, 7B, 7C, and 7D.

FIGS. 7A, 7B, 7C, and 7D are top perspective, alternative top perspective, front elevation, and bottom perspective views, respectively, of a patient-specific cutting guide, or cutting guide 700, according to one alternative embodiment. The cutting guide 700 may be used to correct a bunion deformity, such as that of the foot 200 of FIG. 2. Thus, the cutting guide 700 may also be designed to facilitate resection of the first cuneiform 210 and the first metatarsus 230 with planar cuts at the proper angles to provide dual-plane correction of the orientation of the first metatarsus 230, thereby providing correction in the lateral direction 260 and in the plantar direction 280 or the dorsal direction 290.

As shown, the cutting guide 700 may have a body 710 with a monolithic construction and the general shape of a rectangular prism. The cutting guide 700 may further have a joint alignment feature that helps align the body 710 with the metatarsocuneiform joint between the first cuneiform 210 and the first metatarsus 230. The joint alignment feature may consist of a joint probe 720 that extends from the body 710 and has a blade-like shape. The body 710 may reside on the dorsal surfaces of the first cuneiform 210 and the first metatarsus 230, while the joint probe 720 may protrude into the metatarsocuneiform joint between the first cuneiform 210 and the first metatarsus 230 to provide proper alignment of the body 710 with the metatarsocuneiform joint. Notably, the joint probe 720 may have surfaces that are not simply planar, but rather have some contouring by which the shape of the joint probe 720 is matched to the adjoining surfaces of the first cuneiform 210 and/or the first metatarsus 230. Such contouring of the joint probe 720 may enable more precise alignment of the body 710 with the metatarsocuneiform joint.

The body 710 may have a bone apposition side 730 that, upon attachment of the body 710 to the first cuneiform 210 and the first metatarsus 230, is to face toward the first cuneiform 210 and the first metatarsus 230. The body 710 may also have an outward-facing side 732 that, upon attachment of the body 710 to the first cuneiform 210 and the first metatarsus 230, faces outward, away from the first cuneiform 210 and the first metatarsus 230. Further, the body 710 may have one or more bone attachment features that facilitate attachment of the body 710 to the first cuneiform 210 and/or the first metatarsus 230. Such bone attachment features may comprise any of a wide variety of holes, spikes, fastening devices, and/or the like. As embodied in FIGS. 7A through 7D, the bone attachment features may take the form of holes 740 that extend from the bone apposition side 330 to the outward-facing side 332. The holes 340 may be shaped to accommodate pins, K-wires, and/or other elongated bone fixation elements that can be anchored in the first cuneiform 210 and/or the first metatarsus 230 to keep the cutting guide 700 in place. As embodied in FIGS. 7A through 7D, only one hole 340 may be present on each side of the body 710. Thus, the body 710 may be secured to the first cuneiform 210 with only a single pin or K-wire (not shown) and to the first metatarsus 230 with only another single pin or K-wire (not shown).

The bone apposition side 730 may be custom contoured to match the shapes of the first cuneiform 210 and/or the first metatarsus 230. As embodied in FIGS. 7A through 7D, the bone apposition side 730 may have a cuneiform apposition portion 742 shaped to lie against the dorsal surface of the first cuneiform 210, and a metatarsus apposition portion 744 shaped to lie against the dorsal surface of the first metatarsus 230. As shown, the cuneiform apposition portion 742 may be contoured to match the contour of the dorsal surface of the first cuneiform 210 on which it is to rest, and the metatarsus apposition portion 744 may similarly be contoured to match the contour of the dorsal surface of the first metatarsus 230 on which it is to rest. Thus, the body 710 may have only one stable position and orientation relative to the first cuneiform 210 and the first metatarsus 230.

Like the cuneiform apposition portion 342 and the metatarsus apposition portion 344 of the cutting guide 300, generation of the contours of the cuneiform apposition portion 742 and the metatarsus apposition portion 744 may be performed relative easily in various CAD programs through surface copy operations, Boolean operations, and/or the like.

The body 710 may further have guide features that guide a cutter to resect the first cuneiform 210 and the first metatarsus 230 in the manner needed to make the desired correction. For example, the guide features may be used to guide a planar cutting blade, an arcuate cutting blade, a drill or mill, and/or the like.

In the embodiment of FIGS. 7A through 7D, the guide features may guide a reciprocating planar blade, such as that of a surgical bone saw, that forms planar cuts in the first cuneiform 210 and the first metatarsus 230. Thus, the guide features may take the form of a first slot 750 and a second slot 752, which may be positioned toward the center of the body 710, on opposite sides of the joint probe 720. Thus, upon proper positioning of the cutting guide 700, the first slot 750 may be positioned over the first cuneiform 210 to facilitate resection of the first cuneiform 210, while the second slot 752 may be positioned over the first metatarsus 230 to facilitate resection of the first metatarsus 230.

In operation, the cutting guide 700 may be used in a manner similar to that of the cutting guide 300. However, the cutting guide 700 may only be secured to each of the first cuneiform 210 and the first metatarsus 230 with a single pin or K-wire (not shown), as mentioned previously. Further, the cutting guide 700 is smaller than the cutting guide 300. Thus, the cutting guide 700 may be placed through a smaller, less invasive incision. One advantage to patient-specific instrumentation may be that instruments may be made smaller, since they are not limited to certain sizes. Many known instruments come in discrete sizes, each of which is designed to accommodate a range of patient anatomic dimensions. Thus, for given patient anatomy, the instrument must be large enough to treat the anatomy at either end of its range. This typically requires the instrument to be oversized for many anatomic dimensions it is designed to treat. Notably, the cutting guide 700 is merely one compact example; other cutting guides may be made even smaller; in some embodiments, cutting guides may be made that have a smaller width between holes (e.g., holes 740 on the cutting guide 700). As long as the holes are sufficiently far apart to avoid interference of the pins 500 with the operation of the cutting blade, the cutting guide may function appropriately. Thus, Lapidus and other procedures may be accomplished through a very narrow incision through the use of patient-specific instrumentation.

Those of skill in the art will recognize that a wide variety of differently configured cutting guides may be used in conjunction with the method 120 set forth above. Further, a wide variety of patient-specific instruments may be used in connection with the method 100, including but not limited to cutting guides, gages, implant positioning guides, joint distractors, joint compressors, soft tissue retractors, and the like.

Furthermore, patient-specific cutting guides may be used for various other procedures on the foot, or on other bones of the musculoskeletal system. Patient-specific cutting guides may be used for various procedures involving osteotomy, including but not limited to arthroplasty, fusion, and deformity correction procedures. According to one example, patient-specific cutting guides similar to the cutting guide 300 and the cutting guide 700 may be used for the metatarsophalangeal ("MTP") joint. A method similar to the method 100 may be employed.

In some embodiments, one or more articulating surfaces of a joint may be replaced and/or resurfaced. For example, for the MTP joint, a patient-specific cutting guide may be used to determine the angles of cuts on the distal metatarsus or the proximal phalanx in preparation for replacement or resurfacing of the metatarsal head and/or the proximal phalangeal base. Implants for either the metatarsus or the phalanx may be customized to match the patient's original anatomy, such as the curvature of the MTP joint. In other embodiments, an MTP joint may be fused through the use of patient-specific cutting guides. Patient-specific cutting guides may be used to treat (for example, via fusion, resurfacing, and/or arthroplasty) any joint in the body, using methods similar to the method 100.

According to other examples, patient-specific cutting guides may be used to carry out an Evans calcaneal osteotomy and/or a medializing calcaneal osteotomy. Patient-specific instruments will be shown and described in connection with FIGS. 8A through 11, in relation to an Evans calcaneal osteotomy, and a medializing calcaneal osteotomy.

Figure 8A:
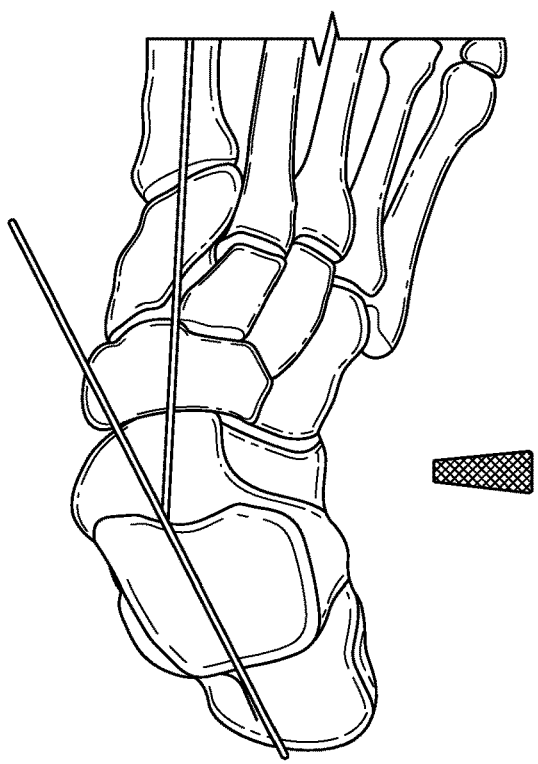
FIGS. 8A, 8B, and 8C are dorsal pre-operative, dorsal post-operative, and lateral post-operative views, respectively, of a foot treated with an Evans calcaneal osteotomy, according to one embodiment.
Figure 8B:
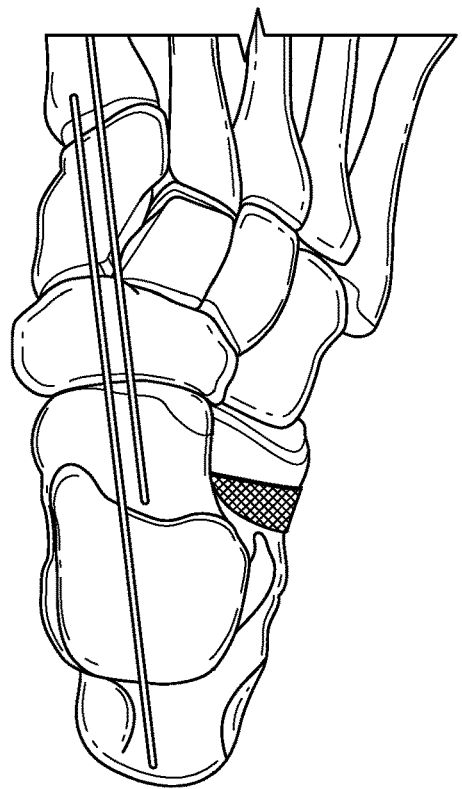
Figure 8C:
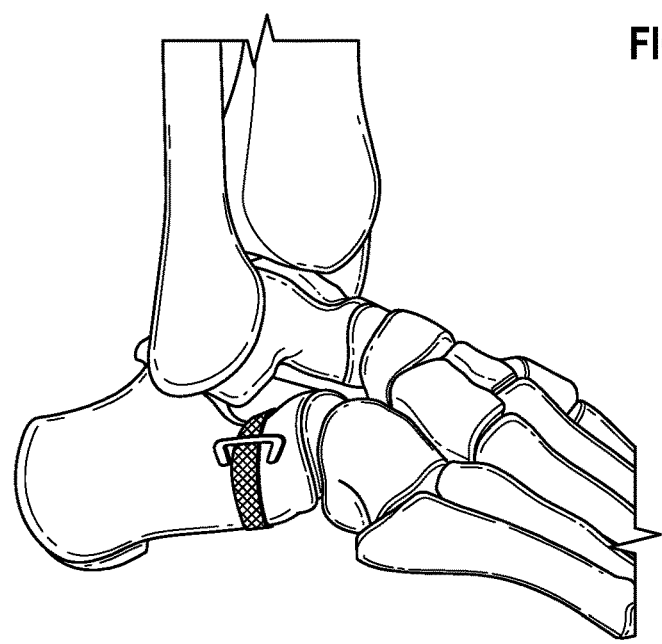

FIGS. 8A, 8B, and 8C are dorsal pre-operative, dorsal post-operative, and lateral post-operative views, respectively, of a foot treated with an Evans calcaneal osteotomy, according to one embodiment. Outward rotation of the foot may occur in patients with flatfoot. An Evans or lateral column lengthening procedure is sometimes performed for these patients. An incision is made on the outside of the foot, and the front half of the heel bone is cut. A bone wedge (typically either titanium or a bone-based graft) is then placed into the cut area of the heel bone. This wedge helps to "lengthen" the heel bone and rotate the foot back into its correct position. The wedge is usually kept in place using screws or a surgical staple.

Figure 9A:
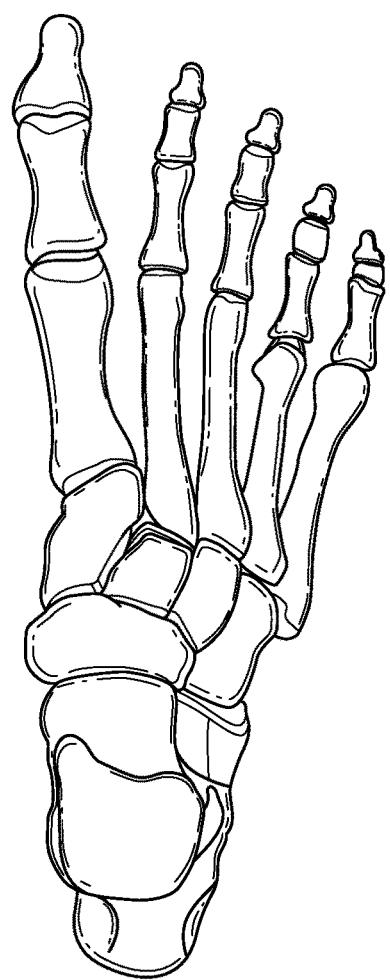
FIGS. 9A and 9B are dorsal post-operative and lateral post-operative views, respectively, of a foot treated with a medializing calcaneal osteotomy, according to one embodiment.
Figure 9B:
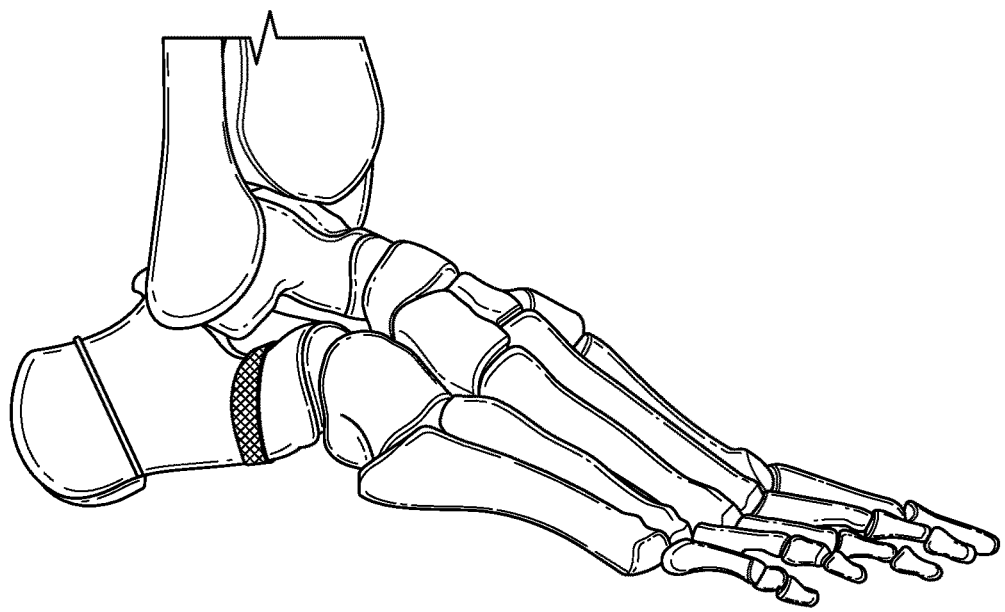

FIGS. 9A and 9B are dorsal post-operative and lateral post-operative views, respectively, of a foot treated with a medializing calcaneal osteotomy, according to one embodiment. A medializing calcaneal osteotomy (heel slide) procedure is often used when the calcaneus (heel bone) has shifted out from underneath the leg. An incision is made on the outside of the heel, and the back half of the heel bone is cut and slid back underneath the leg. The heel is then fixed in place using metal screws or a plate. This also helps to reposition the Achilles tendon towards the center of the ankle/rearfoot. The medializing calcaneal osteotomy can be used in place of, or in addition to, an Evans calcaneal osteotomy.

Figure 10:
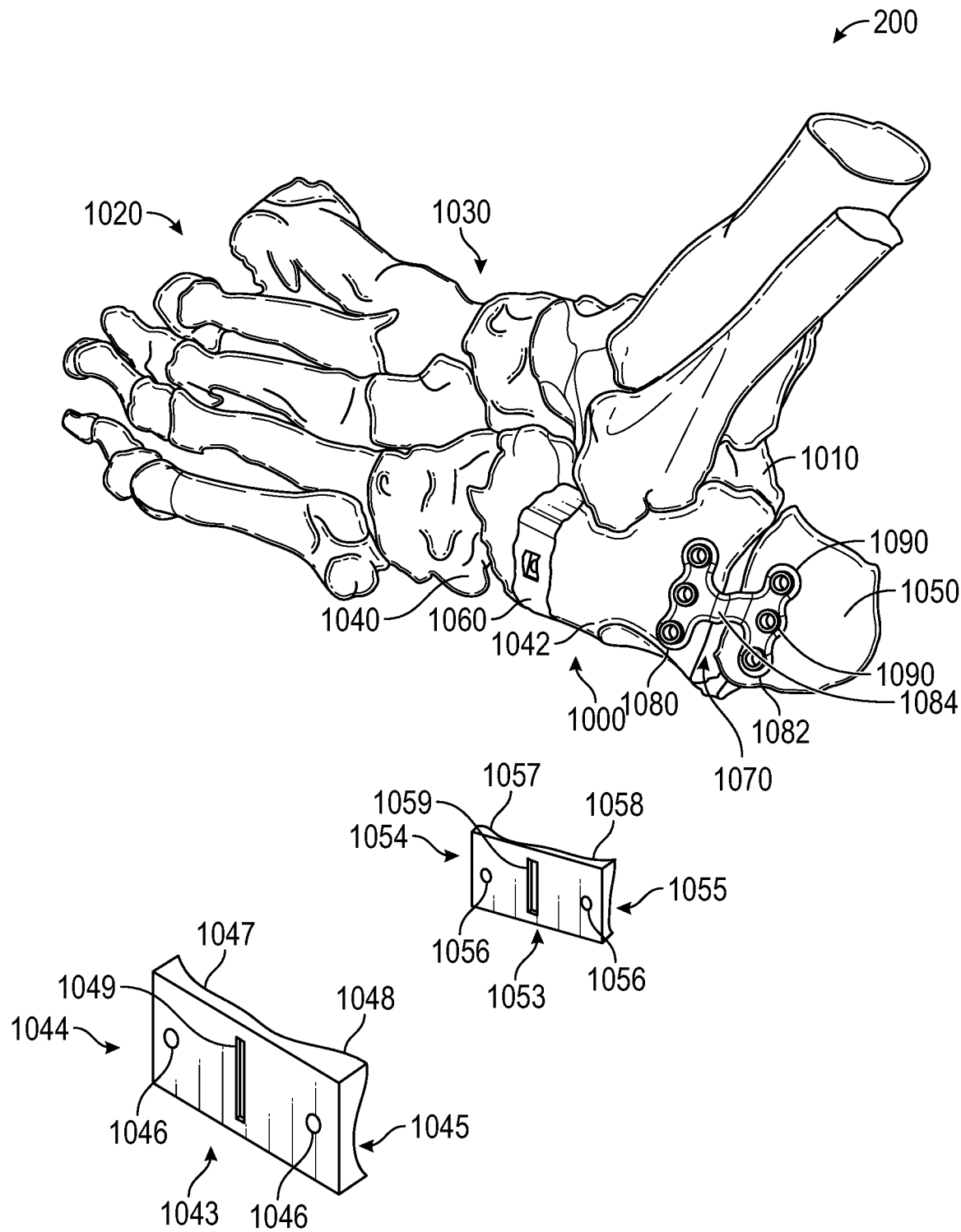
FIG. 10 is a rear, perspective view of the foot of FIG. 2, after performance of an Evans calcaneal osteotomy and a medializing calcaneal osteotomy with patient-specific instruments and/or implants, according to one embodiment.

FIG. 10 is a rear, perspective view of the foot 200 of FIG. 2, after performance of an Evans calcaneal osteotomy and a medializing calcaneal osteotomy with patient-specific instruments and/or implants, according to one embodiment. The foot 200 may have a calcaneus 1000 and a talus 1010, in addition to the metacarpals 1020 and cuneiforms 1030 depicted in FIG. 2. Pursuant to the Evans calcaneal osteotomy, an anterior portion of the calcaneus 1000 may be cut along the medial-lateral direction to separate a first bone segment 1040 of the calcaneus 1000 from a second bone segment 1042 of the calcaneus 1000. The second bone segment 1042 may be reoriented medially, relative to the first bone segment 1040, such that a heel 1050 of the calcaneus 1000 is moved medially, simulating a natural, healthy arch in the foot 200.

The cut between the first bone segment 1040 and the second bone segment 1042 may be carried out virtually (for example, in CAD) on a model of the calcaneus 1000 obtained from a CT scan or other imaging of the patient's foot. Thus, the optimal realignment of the posterior end of the calcaneus 1000 can be obtained. If desired, a patient-specific cutting guide, or cutting guide 1043, may be generated in order to facilitate resection of the calcaneus 1000.

As shown, the cutting guide 1043 may have a first end 1044 and a second end 1045, each of which has a bone attachment feature 1046. The bone attachment features 1046 may be used to secure the first end 1044 and the second end 1045 to the first bone segment 1040 and the second bone segment 1042, respectively. The first end 1044 may have a first bone engagement surface 1047 that is shaped to match a corresponding contour on the first bone segment 1040, and the second end 1045 may have a second bone engagement surface 1048 that is shaped to match a corresponding contour on the second bone segment 1042. Thus, the cutting guide 1043 may naturally lie flush with the surface of the calcaneus 1000, in the optimal position on the calcaneus 1000 to facilitate resection of the calcaneus 1000 to divide the first bone segment 1040 from the second bone segment 1042. The cutting guide 1043 may have a guide feature 1049, such as a slot, that can be used to guide a cutter to form a single cut between the first bone segment 1040 and the second bone segment 1042.

After the cut has been made to split the calcaneus 1000 into the first bone segment 1040 and the second bone segment 1042, the surgeon may angle the second bone segment 1042 relative to the first bone segment 1040 in the predetermined (previously modeled) relative orientation. This reorientation between the first bone segment 1040 and the second bone segment 1042 may leave a wedge-shaped gap between the first bone segment 1040 and the second bone segment 1042. In order to maintain the desired relative orientation, an implant 1060 with a wedge shape may be inserted into the gap and secured to the first bone segment 1040 and the second bone segment 1042. The implant 1060 may be fabricated specifically for the patient, since the precise angulation and position of the realignment may also be patient specific. As shown, the implant 1060 may have exterior surfaces that are contoured to match the contours of the adjoining portions of the first bone segment 1040 and the second bone segment 1042. Thus, the implant 1060 may provide secure fixation, while not protrude beyond the adjoining surfaces of the first bone segment 1040 and the second bone segment 1042. Thus, the implant 1060 may be devoid of proud edges or other protrusions that could otherwise interfere with motion between the calcaneus 1000 and the talus 1010, or with surrounding soft tissues, thus interfering with the patient's post-operative gait.

The implant 1060 may be made of any biocompatible material, including but not limited to Titanium and alloys thereof, stainless steel, PEEK, and/or the like. The implant 1060 may be formed by any method known in the art, including but not limited to forging, casting, milling, additive manufacturing, and/or the like. In some embodiments, the implant 1060 may have an interior void that can be filled with bone graft or other material designed to promote boney in-growth between the cut surfaces of the first bone segment 1040 and the second bone segment 1042. In alternative embodiments, the implant 1060 may have a mesh and/or lattice structure that facilitates such boney in-growth, which structure may be formed via additive manufacturing.

As mentioned previously, a medializing calcaneal osteotomy may optionally be performed in addition to or in place of the Evans calcaneal osteotomy. As shown, the heel 1050 may be cut from the remainder of the second bone segment 1042 and may be displaced medially. This displacement may also help to restore normal gait and tendon function in the foot 200, particularly when coupled with the Evans calcaneal osteotomy. The proper displacement of the heel 1050 relative to the remainder of the second bone segment 1042 may be determined based on analysis of the CAD models from scans of the foot 200. If desired, the model of the calcaneus 1000 may be divided and manipulated in CAD to simulate the repositioning of the heel 1050 pursuant to the medializing calcaneal osteotomy. Thus, the alignment of the heel 1050 relative to the remainder of the foot 200 can easily be assessed and optimized prior to surgery.

Such preoperative alignment and planning may be particularly useful where multiple procedures, such as the Evans calcaneal osteotomy and the medializing calcaneal osteotomy, are combined for a single patient. Without such planning, it may be difficult to properly assess the effect of the combined procedures on the patient's anatomy. For example, the effect of the Evans calcaneal osteotomy, and that of the medializing calcaneal osteotomy, is to shift the heel 1050 medially. The combined shift may be difficult to assess in the operating room but may be much more easily and accurately gauged via manipulation of the modeled anatomy.

In some embodiments, one or more additional procedures may be carried out, in addition to or in the alternative to those of FIG. 9. For example, in addition to or in the alternative to the Evans calcaneal osteotomy and the medializing calcaneal osteotomy, a cotton osteotomy and/or a first metatarsal midfoot osteotomy may be performed. Patient-specific cutting guides may be designed, fabricated, and surgically used to facilitate any of these procedures through the presence of bone engagement surfaces that are shaped to rest on the particular bony surfaces adjacent to the osteotomy.

As in the case of the Evans calcaneal osteotomy, a custom cutting guide, or cutting guide 1053, may be generated to help the surgeon obtain the correction that was previously modeled and/or planned using the computer models of the foot 200. The cutting guide may 1053 have a structure and function similar to that of the cutting guide 1043 used for the Evans calcaneal osteotomy. Such a cutting guide may have contoured surfaces that match the contours of the adjoining boney surfaces of the remainder of the second bone segment 1042 and/or the heel 1050.

More specifically, the cutting guide 1053 may have a first end 1054 and a second end 1055, each of which has a bone attachment feature 1056. The bone attachment features 1056 may be used to secure the first end 1054 and the second end 1055 to the second bone segment 1042 and the heel 1050, respectively. The first end 1054 may have a first bone engagement surface 1057 that is shaped to match a corresponding contour on the second bone segment 1042, and the second end 1055 may have a second bone engagement surface 1058 that is shaped to match a corresponding contour on the heel 1050. Thus, the cutting guide 1053 may naturally lie flush with the surface of the calcaneus 1000, in the optimal position on the calcaneus 1000 to facilitate resection of the calcaneus 1000 to divide the second bone segment 1042 from the heel 1050. The cutting guide 1053 may have a guide feature 1059, such as a slot, that can be used to guide a cutter to form a single cut between the second bone segment 1042 and the heel 1050.

In order to maintain the heel 1050 in the proper position relative to the remainder of the second bone segment 1042, a bone plate 1070 may be secured to the heel 1050 and to the remainder of the second bone segment 1042. The bone plate 1070 may include a first end 1080 secured to the remainder of the second bone segment 1042, a second end 1082 secured to the heel 1050, and an intermediate portion 1084 that extends from the first end 1080 to the second end 1082, and provides the desired medial shift between the first end 1080 and the second end 1082. The first end 1080 and the second end 1082 may be secured to the remainder of the second bone segment 1042 and to the heel 1050, respectively, through the use of screws 1090.

Like the implant 1060, the bone plate 1070 may be made of any known biocompatible material, through the use of any manufacturing process known in the art. In some embodiments, the bone plate 1070 may also be fabricated specifically for the foot 200, enabling the bone plate 1070 to maintain precisely the desired level of correction. When made specifically for the foot 200 in combination with each other, the implant 1060 and the bone plate 1070 may provide a highly predictable, precise, and customizable level of correction of the flat foot deformity.

Figure 11:
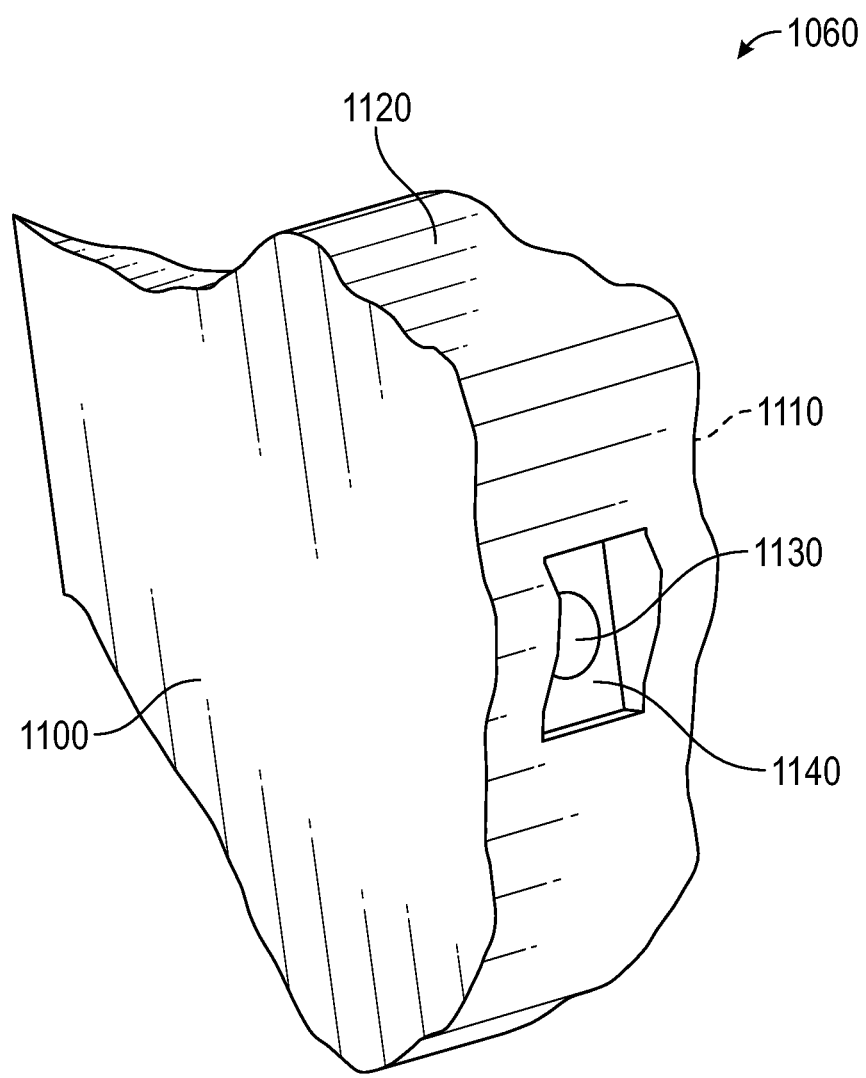
FIG. 11 is a perspective view of the implant of FIG. 10, in isolation, according to one embodiment.

FIG. 11 is a perspective view of the implant 1060, in isolation. As shown, the implant 1060 may have a first bone-facing surface 1100 that is generally flat and shaped to match the cut surface of the first bone segment 1040. The first bone-facing surface 1100 is shown in FIG. 11 with a smooth shape; however, in alternative embodiments, the first bone-facing surface 1100 may be roughened and/or may have teeth, spikes, ridges, and/or other features intended to penetrate the first bone segment 1040 in order to provide for more secure engagement of the implant 1060 with the first bone segment 1040. Similarly, the implant 1060 may have a second bone-facing surface 1110 (not visible) that is also generally flat and shaped to match the cut surface of the second bone segment 1042. Like the first bone-facing surface 1100, the second bone-facing surface 1110 may be roughened or have protruding features that strengthen engagement of the implant 1060 with the second bone segment 1042. If desired, the implant 1060 may be further held in place through the use of bone screws, cement, one or more bone plates, and/or other features known in the art to secure an implant to bone.

The edges of the first bone-facing surface 1100 and the second bone-facing surface 1110 may be shaped to line up with the edges of the cut surfaces of the first bone segment 1040 and the second bone segment 1042, respectively. The implant 1060 may also have a contoured surface 1120 that extends between the edges of the first bone-facing surface 1100 and the second bone-facing surface 1110. The contoured surface 1120 may also be contoured to match the contours of the adjoining portions of the first bone segment 1040 and the second bone segment 1042. Thus, the contoured surface 1120 may provide a continuous surface, devoid of protrusions, that extends between the adjoining surfaces of the first bone segment 1040 and the second bone segment 1042.

A threaded hole 1130 may optionally be provided in the contoured surface 1120. The threaded hole 1130 may be used to secure the implant 1060 to an insertion instrument, a positioning instrument, and/or a removal instrument. The threaded hole 1130 may be formed in a recess 1140 in the contoured surface 1120 so that the threaded hole 1130 can have the desired orientation, without affecting the shape of the contoured surface 1120 more than necessary. Of course, many other features may be used to secure an instrument to the implant 1060, including various clips, clamps, fasteners, and interfacing features, as known in the art.

The present disclosure is not limited to cutting guides or extremity procedures. In some embodiments, patient-specific instrumentation may be used to correct a wide variety of bone conditions. Such conditions include, but are not limited to, any angular deformities from within one bone segment in either the lower or upper extremities (for example, tibial deformities, calcaneal deformities, femoral deformities, and radial deformities). The present disclosure may also be used to treat an interface between two bone segments (for example, the ankle joint, metatarsal cuneiform joint, lisfranc's joint, complex charcot deformity, wrist joint, knee joint, etc.). As one example, an angular deformity or segmental malalignment in the forefoot may be treated, such as is found at the metatarsal cuneiform level, the midfoot level such as the navicular cuneiform junction, hindfoot at the calcaneal cubiod or subtalar joint or at the ankle between the tibia and talar junction. Additionally, patient-specific instruments could be used in the proximal leg between two bone segments or in the upper extremity such as found at the wrist or metacarpal levels.

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

Reference throughout this specification to "an embodiment" or "the embodiment" means that a particular feature, structure or characteristic described in connection with that embodiment is included in at least one embodiment. Thus, the quoted phrases, or variations thereof, as recited throughout this specification are not necessarily all referring to the same embodiment.

Similarly, it should be appreciated that in the above description of embodiments, various features are sometimes grouped together in a single embodiment, Figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

Recitation in the claims of the term "first" with respect to a feature or element does not necessarily imply the existence of a second or additional such feature or element. Elements recited in means-plus-function format are intended to be construed in accordance with 35 U.S.C. § 112 Para. 6. It will be apparent to those having skill in the art that changes may be made to the details of the above-described embodiments without departing from the underlying principles set forth herein.

While specific embodiments and applications of the present disclosure have been illustrated and described, it is to be understood that the scope of this disclosure is not limited to the precise configuration and components disclosed herein. Various modifications, changes, and variations which will be apparent to those skilled in the art may be made in the arrangement, operation, and details of the methods and systems of the present disclosure set forth herein without departing from it spirit and scope.

What is claimed is:

1. A method for correcting a bunion present in a patient's foot, the method comprising:
   obtaining a first bone model of a cuneiform of the patient's foot;
   obtaining a second bone model of a metatarsus of the patient's foot;
   virtually repositioning the second bone model relative to the first bone model to simulate
   reorientation of the metatarsus relative to the cuneiform to correct the bunion; and using at least the first bone model relative to the repositioned second bone model to generate a cutting guide model defining:
a first bone engagement surface shaped to match a first contour on the cuneiform;
a second bone engagement surface shaped to match a second contour of the metatarsus; and
a first guide feature that, with the first bone engagement surface overlying the first contour, is positioned to guide resection of at least one of the cuneiform and the metatarsus as part of a bunion correction osteotomy for correcting the bunion.

2. The method of claim 1, wherein:
the first guide feature is positioned to guide resection of the cuneiform; and
the cutting guide model further defines:
a second guide feature that, with the second bone engagement surface overlying the second contour, is positioned to guide resection of the metatarsus.

3. The method of claim 2, wherein the cutting guide model further comprises:
a first end having the first bone engagement surface;
a second end having the second bone engagement surface;
a first bone attachment feature positioned to secure the first end to the cuneiform; and
a second bone attachment feature positioned to secure the second end to the metatarsus.

4. The method of claim 3, further comprising:
using the cutting guide model to fabricate a cutting guide having the first bone engagement surface, the second bone engagement surface, the first bone attachment feature, the second bone attachment feature, the first guide feature, and the second guide feature.

5. The method of claim 4, further comprising:
placing the cutting guide such that the first bone engagement surface overlies the first contour and the second bone engagement surface overlies the second contour;
securing the first bone attachment feature to the cuneiform;
securing the second bone attachment feature to the metatarsus;
with the first guide feature, guiding motion of a cutter to resect the cuneiform; and
with the second guide feature, guiding motion of a cutter to resect the metatarsus.

6. The method of claim 5, further comprising:
reorienting the metatarsus relative to the cuneiform; and
after reorienting the metatarsus relative to the cuneiform, promoting fusion between the cuneiform and the metatarsus.

7. The method of claim 1, wherein:
obtaining the first bone model comprises obtaining CT scan data of the cuneiform; and
using the first bone model to generate the cutting guide model comprises:
converting the CT scan data to a CAD models;
using the CAD model to obtain the first contour; and
using the first contour to generate the first bone engagement surface of the cutting guide model.

8. The method of claim 1, further comprising using at least the first bone model to generate an implant model defining a first bone-facing surface comprising a first shape that matches a first profile of a first resected surface with a cutting guide fabricated using the cutting guide model.

9. The method of claim 8, wherein the implant model further comprises a second bone-facing surface comprising a second shape that matches a second profile of a second resected surface of the cuneiform or the metatarsus after resection with the cutting guide.

10. The method of claim 9, further comprising:
using the cutting guide model to fabricate a cutting guide having the first bone engagement surface and first guide feature;
using the implant model to fabricate an implant having the first bone-facing surface and the second bone-facing surface;
placing the cutting guide such that the first bone engagement surface overlies the first contour;
with at least the first guide feature, guiding motion of a cutter to resect at least one of the cuneiform or the metatarsus to define the first resected surface and the second resected surface; and
placing the implant between the first resected surface and the second resected surface such that the first shape is aligned with the first profile and the second shape is aligned with the second profile.

* * * * *